US011725007B2

(12) United States Patent
Accetta et al.

(10) Patent No.: US 11,725,007 B2
(45) Date of Patent: Aug. 15, 2023

(54) META TYROSINE DERIVATIVES AS RHO-KINASE INHIBITORS

(71) Applicant: Chiesi Farmaceutici S.p.A., Parma (IT)

(72) Inventors: Alessandro Accetta, Parma (IT); Fabio Rancati, Parma (IT); Christine Edwards, Parma (IT); Gurdip Bhalay, Parma (IT); Patrizia Tisselli, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 567 days.

(21) Appl. No.: 16/954,964

(22) PCT Filed: Dec. 12, 2018

(86) PCT No.: PCT/EP2018/084536
§ 371 (c)(1),
(2) Date: Jun. 17, 2020

(87) PCT Pub. No.: WO2019/121223
PCT Pub. Date: Jun. 27, 2019

(65) Prior Publication Data
US 2020/0377500 A1 Dec. 3, 2020

(30) Foreign Application Priority Data
Dec. 18, 2017 (EP) .................................... 17208186

(51) Int. Cl.
| | | |
|---|---|---|
| *C07D 471/04* | (2006.01) | |
| *A61K 9/00* | (2006.01) | |
| *A61K 31/407* | (2006.01) | |
| *A61K 31/496* | (2006.01) | |
| *A61K 45/06* | (2006.01) | |

(52) U.S. Cl.
CPC ............ *C07D 471/04* (2013.01); *A61K 9/008* (2013.01); *A61K 9/0075* (2013.01); *A61K 9/0078* (2013.01); *A61K 31/407* (2013.01); *A61K 31/496* (2013.01); *A61K 45/06* (2013.01)

(58) Field of Classification Search
CPC .................................................. C07D 471/04
See application file for complete search history.

(56) References Cited

U.S. PATENT DOCUMENTS

2006/0241127 A1 10/2006 Feurer et al.
2008/0139595 A1 6/2008 Schirok et al.

FOREIGN PATENT DOCUMENTS

| WO | WO 2004/039796 A1 | 5/2004 |
| WO | WO 2005/097790 A1 | 10/2005 |
| WO | WO 2006/009889 A1 | 1/2006 |
| WO | WO 2009/079008 A1 | 6/2009 |
| WO | WO 2010/032875 A2 | 3/2010 |
| WO | WO 2012/007539 A1 | 1/2012 |
| WO | WO 2014/118133 A1 | 8/2014 |
| WO | WO 2018/115383 A1 | 6/2018 |
| WO | WO 2018/138293 A1 | 8/2018 |

OTHER PUBLICATIONS

Duong-Quy, S., et al., "Role of Rho-kinase and Its Inhibitors in Pulmonary Hypertension," *Pharmacol Ther.*, 137(3):352-64, Elsevier, Netherlands (2013).
Fernandes, L.B., et al., "Rho-kinase as a therapeutic target in the treatment of asthma and chronic obstructive pulmonary disease," *Ther Adv Respir Dis.*, 1 (1):25-33, SAGE Publishings, United States (2007).
Gosens, R., et al., "Rho-kinase as a Drug Target for the Treatment of Airway Hyperrespon-Siveness in Asthma," *Mini-Rev. Med. Chem.*, 2006, 6(3):339-348, Bentham Science Publishers, United Arab Emirates (2006).
International Search Report and Written Opinion for International Application No. PCT/EP2018/084536, European Patent Office, Netherlands, dated May 22, 2019, 8 pages.
Jiang, C., et al., "Fasudil, a Rho-Kinase Inhibitor, Attenuates Bleomycin-Induced Pulmonary Fibrosis in Mice," *Int. J. Mol. Sci.*, 13(7):8293-8307, MDPI, Switzerland (2012).
Riento, K. and Ridley, A. J., "Rocks: Multifunctional Kinases in Cell Behavior," *Nat. Rev. Mol. Cell Biol.*, 4(6), 446-456, Springer Nature Limited, Germany (2003).

*Primary Examiner* — Yong S. Chong
(74) *Attorney, Agent, or Firm* — Sterne, Kessler, Goldstein & Fox P.L.L.C.

(57) ABSTRACT

The invention relates to compounds of formula (I) inhibiting Rho Kinase that are meta tyrosine derivatives, processes for preparing such compounds, pharmaceutical compositions containing them and therapeutic use thereof. Particularly the compounds of the invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

13 Claims, No Drawings

META TYROSINE DERIVATIVES AS RHO-KINASE INHIBITORS

FIELD OF THE INVENTION

The present invention relates to compounds inhibiting Rho Kinase (hereinafter ROCK Inhibitors); particularly the invention relates to meta tyrosine derivatives, processes for preparing such compounds, pharmaceutical compositions containing them and therapeutic use thereof.

The compounds of the invention are inhibitors of the activity or function of the ROCK-I and/or ROCK-II isoforms of the Rho-associated coiled-coil forming protein kinase (ROCK).

Therefore, the compounds of the invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

BACKGROUND OF THE INVENTION

Rho-associated coiled-coil forming protein kinase (ROCK) belongs to the AGC (PKA/PKG/PKC) family of serine-threonine kinases. Two human isoforms of ROCK have been described. ROCK-I (also referred to as p160 ROCK or ROKβ) and ROCK-II (ROKα) are approximately 160 kDa proteins containing an N-terminal Ser/Thr kinase domain, followed by a coiled-coil structure, a pleckstrin homology domain, and a cysteine-rich region at the C-terminus (Riento, K.; Ridley, A. J. Rocks: multifunctional kinases in cell behaviour. Nat. Rev. Mol. Cell Biol. 2003, 4, 446-456).

Both ROCK-II and ROCK-I are expressed in many human and rodent tissues including the heart, pancreas, lung, liver, skeletal muscle, kidney and brain (Riento and Ridley, 2003 In patients with pulmonary hypertension, ROCK activity is significantly higher in both lung tissues and circulating neutrophils as compared with controls (Duong-Quy S, Bei Y, Liu Z, Dinh-Xuan A T. Role of Rho-kinase and its inhibitors in pulmonary hypertension. Pharmacol Ther. 2013; 137(3):352-64). A significant correlation was established between neutrophil ROCK activity and the severity and duration of pulmonary hypertension (Duong-Quy et al., 2013).

There is now substantial evidence that ROCK is involved in many of the pathways that contribute to the pathologies associated with several acute and chronic pulmonary diseases, including asthma, COPD, bronchiectasis and ARDS/ALI. Given the biological effect of ROCK, selective inhibitors have the potential to treat a number of pathological mechanisms in respiratory diseases, such as smooth muscle hyper-reactivity, bronchoconstriction, airway inflammation and airway remodeling, neuromodulation and exacerbations due to respiratory tract viral infection (Fernandes L B, Henry P J, Goldie R G. Rho kinase as a therapeutic target in the treatment of asthma and chronic obstructive pulmonary disease. Ther Adv Respir Dis. 2007 October; 1(1):25-33). Indeed the Rho kinase inhibitor Y-27632 causes bronchodilatation and reduces pulmonary eosinophilia trafficking and airways hyperresponsiveness (Gosens, R.; Schaafsma, D.; Nelemans, S. A.; Halayko, A. J. Rhokinase as a drug target for the treatment of airway hyperresponsiveness in asthma. Mini-Rev. Med. Chem. 2006, 6, 339-348). Pulmonary ROCK activation has been demonstrated in humans with idiopathic pulmonary fibrosis (IPF) and in animal models of this disease. ROCK inhibitors can prevent fibrosis in these models, and more importantly, induce the regression of already established fibrosis, thus indicating ROCK inhibitors as potential powerful pharmacological agents to halt progression of pulmonary fibrosis (Jiang, C.; Huang, H.; Liu, J.; Wang, Y.; Lu, Z.; Xu, Z. Fasudil, a rho-kinase inhibitor, attenuates bleomycin-induced pulmonary fibrosis in mice. Int. J. Mol. Sci. 2012, 13, 8293-8307).

Various compounds have been described in the literature as Rho Kinase Inhibitors. See e.g. WO2004/039796; WO2006/009889; WO2010/032875; WO2009/079008; WO2014/118133, and from the same Applicant WO 2018/115383 and WO 2018/138293.

A potential remains for developing novel and pharmacologically improved ROCK inhibitors in many therapeutic areas such as: cardiovascular and respiratory diseases, erectile dysfunction, fibrotic diseases, insulin resistance, kidney failure, central nervous system disorders, auto-immune diseases and oncology.

In view of the number of pathological responses which are mediated by ROCK enzymes, there is a continuing need for inhibitors of such enzymes which can be useful in the treatment of many disorders. The invention relates to novel compounds which are inhibitors of ROCK-I and ROCK-II isoforms of the Rho-associated coiled-coil forming protein kinase (ROCK), as demonstrated by the pharmacological activity data reported. Furthermore the compounds of the invention have therapeutically desirable characteristics, that makes them particularly suitable to be administered also by inhalation for the treatment of respiratory disease. The compounds of the invention are particularly promising for some pulmonary diseases including asthma, chronic obstructive pulmonary disease (COPD), idiopathic pulmonary fibrosis (IPF) and pulmonary hypertension (PH) and specifically pulmonary arterial hypertension (PAH).

SUMMARY OF THE INVENTION

The present invention is directed to compounds of formula (I)

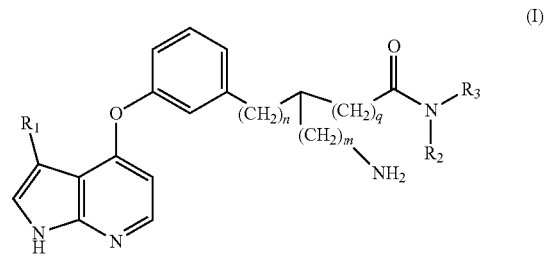

wherein $R_1$, $R_2$, $R_3$, n, m and q are as reported below in the detailed description of the invention, acting as ROCK inhibitors, to processes for the preparation thereof, pharmaceutical compositions comprising them either alone or in combination with one or more active ingredient, in admixture with one or more pharmaceutically acceptable carrier.

In one aspect, the invention provides the use of a compound of formula (I) for the manufacture of a medicament.

In a further aspect, the invention provides the use of a compound of formula (I) for the preparation of a medicament for the treatment of any disease characterized by ROCK enzyme aberrant activity and/or wherein an inhibition of activity is desirable and in particular through the selective inhibition of the ROCK enzyme isoforms over other Kinases.

Moreover the invention provides a method for prevention and/or treatment of any disease wherein a ROCK enzyme inhibition is desirable, said method comprises administering to a patient in need of such treatment a therapeutically effective amount of a compound of formula (I).

In particular the compounds of the invention alone or combined with other active ingredients may be administered for the prevention and/or treatment of a pulmonary disease including asthma, chronic obstructive pulmonary disease (COPD), idiopathic pulmonary fibrosis (IPF) and pulmonary hypertension (PH) and specifically pulmonary arterial hypertension (PAH).

DETAILED DESCRIPTION OF THE INVENTION

The invention relates to compounds of formula (I)

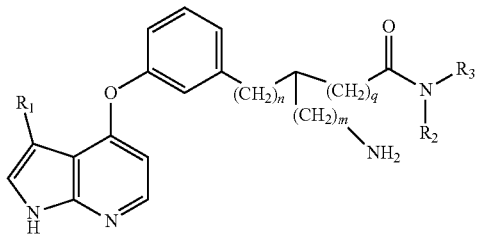

(I)

wherein n, q and m are zero or an integer from 1 to 2;
$R_1$ is selected from the group consisting of:
—H,
halogen,
—CN,
$(C_1-C_6)$ alkyl,
$R_2$ and $R_3$, the same or different, are selected from the group consisting of:
—H,
$(C_1-C_6)$ alkyl,
$(C_1-C_6)$ haloalkyl,
$(C_1-C_6)$ hydroxyalkyl,
$(C_1-C_6)$ aminoalkyl,
$(C_1-C_6)$ alkoxy $(C_1-C_6)$ alkyl,
heteroaryl$(C_1-C_6)$alkyl,
each of said heteroaryl is further optionally substituted by one or more group independently selected from halogen, —CN, —OH, $(C_1-C_8)$alkyl, $(C_1-C_6)$ haloalkyl, $(C_1-C_{10})$ alkoxy, aryl, aryl$(C_1-C_6)$alkyl, carbamoyl, $(C_1-C_6)$ aminoalkyl, $(C_1-C_6)$ hydroxyalkyl; or alternatively, $R_2$ and $R_3$, taken together with the nitrogen atom they are linked to, form a mono-cyclic saturated or partially saturated heterocyclic radical, wherein at least one further ring carbon atom is optionally replaced by N, said heterocyclic radical being optionally in its turn further substituted with one or more $(C_1-C_6)$ alkyl groups;

or pharmaceutically acceptable salts and solvates thereof.

Definitions

The term "pharmaceutically acceptable salts" refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "halogen" or "halogen atoms" includes fluorine, chlorine, bromine, and iodine atom, preferably chlorine or fluorine.

The term "$(C_1-C_6)$ alkyl" refers to straight-chained or branched alkyl groups wherein the number of carbon atoms is in the range 1 to 6. Particular alkyl groups are methyl, ethyl, n-propyl, isopropyl and t-butyl.

The expressions "$(C_1-C_6)$ haloalkyl" refer to the above defined "$(C_1-C_6)$alkyl" groups wherein one or more hydrogen atoms are replaced by one or more halogen atoms, which can be the same or different.

Examples of said $(C_1-C_6)$ haloalkyl groups may thus include halogenated, poly-halogenated and fully halogenated alkyl groups wherein all of the hydrogen atoms are replaced by halogen atoms, e.g. trifluoromethyl or difluoro methyl groups.

By way of analogy, the terms "$(C_1-C_6)$ hydroxyalkyl" or "$(C_1-C_6)$ aminoalkyl" refer to the above defined "$(C_1-C_6)$ alkyl" groups wherein one or more hydrogen atoms are replaced by one or more hydroxy (OH) or amino group respectively. Examples include respectively hydroxymethyl, aminomethyl, dimethylaminopropyl and the like.

In the present description, unless otherwise provided, the definition of aminoalkyl encompasses alkyl groups (i.e. "$(C_1-C_6)$ alkyl" groups) substituted by one or more amino group ($NR_7R_8$). Thus, an example of aminoalkyl is a monoaminoalkyl group such as $R_7R_8N$—$(C_1-C_6)$ alkyl.

With reference to the substituent $R_7$ and $R_8$ as defined above and below, when $R_7$ and $R_8$ are taken together with the nitrogen atom they are linked to form a 4 to 6 membered heterocyclic radical, at least one further ring carbon atom in said heterocyclic radical is optionally replaced by at least one heteroatom (e.g. N, S or O) and/or may bear -oxo (=O) substituent groups. It is understood that said heterocyclic radical might be further optionally substituted on any available position in the ring, namely on a carbon atom, or on any heteroatom available for substitution. Substitution on a carbon atom includes spiro disubstitution as well as substitution on two adjacent carbon atoms, in both cases thus form an additional 5 to 6 membered heterocyclic ring. Examples of said heterocycle radicals are 1-pyrrolidinyl, 1-piperidinyl, 1-piperazinyl, 4-morpholinyl, piperazin-4-yl-2-one, 4-methylpiperazine-1-yl, 4-metylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, (3aR,6aS)-5-methyl-octahydropyrrolo[3,4-c]pyrrol-2-yl, 8-methyl-2,8-diazaspiro[4.5]decane-2-yl, 5-methyloctahydropyrrolo[3,4-c]pyrrole-2-yl, 1,1-dioxidothiomorpholin-4-yl.

The term "$(C_3-C_{10})$ cycloalkyl" likewise "$(C_3-C_6)$ cycloalkyl" refers to saturated cyclic hydrocarbon groups containing the indicated number of ring carbon atoms. Examples include cyclopropyl, cyclobutyl, cyclopentyl, cyclohexyl, cycloheptyl, and polycyclic ring systems such as adamantan-yl.

The term "$(C_2-C_6)$ alkenyl" refers to straight or branched carbon chains with one or more double bonds, conjugated or not conjugated, in cis or trans configuration, wherein the number atoms is in the range 2 to 6.

By way of analogy, the terms "$(C_5-C_7)$ cycloalkenyl" refers to cyclic hydrocarbon groups containing from 5 to 7 ring carbon atoms and one or two double bonds.

The term "$(C_2-C_6)$ alkynyl" refers to straight or branched carbon chains with one or more triple bonds wherein the number atoms is in the range 2 to 6.

The term "$(C_2-C_6)$ hydroxyalkynyl" refers to the above defined "$(C_1-C_6)$ alkynyl" groups wherein one or more hydrogen atoms are replaced by one or more hydroxy (OH) group.

The term "$(C_2-C_6)$ aminoalkynyl" refers to the above defined "$(C_1-C_6)$ alkynyl" groups wherein one or more hydrogen atoms are replaced by one or more ($-NR_7R_8$) groups.

The expression "aryl" refers to mono, bi- or tri-cyclic carbon ring systems which have 6 to 20, preferably from 6 to 15 ring atoms, wherein at least one ring is aromatic. The expression "heteroaryl" refers to mono-, bi- or tri-cyclic ring systems with 5 to 20, preferably from 5 to 15 ring atoms, in which at least one ring is aromatic and in which at least one ring atom is a heteroatom (e.g. N, S or O).

Examples of suitable aryl or heteroaryl monocyclic ring systems include, for instance, phenyl, thienyl, pyrrolyl, pyrazolyl, imidazolyl, isoxazolyl, oxazolyl, isothiazolyl, thiazolyl, pyridinyl, pyrimidinyl, pyrazinyl, triazinyl, furanyl radicals and the like.

Examples of suitable aryl or heteroaryl bicyclic ring systems include naphthalenyl, biphenylenyl, purinyl, pteridinyl, pyrazolopyrimidinyl, benzotriazolyl, benzoimidazole-yl, quinolinyl, isoquinolinyl, indolyl, isoindolyl, benzothiopheneyl, benzodioxinyl, dihydrobenzodioxinyl, indenyl, dihydro-indenyl, dihydrobenzo[1,4]dioxinyl, benzothiazole-2-yl, dihydrobenzodioxepinyl, benzooxazinyl radicals and the like.

Examples of suitable aryl or heteroaryl tricyclic ring systems include fluorenyl radicals as well as benzocondensed derivatives of the aforementioned heteroaryl bicyclic ring systems.

In an analogous manner, the expressions "arylene" and "heteroarylene" refer to divalent groups, such a phenylene, biphenylene and thienylene. Such groups are also commonly named as "arenediyl" or "heteroarenediyl" groups. For example o-phenylene is also named benzene-1,2-diyl. Thienyl-ene is alternatively named thiophenediyl.

The expression "$(C_3-C_6)$ heterocycloalkyl" refers to saturated or partially unsaturated monocyclic $(C_3-C_6)$ cycloalkyl groups in which at least one ring carbon atom is replaced by at least one heteroatom (e.g. N, S or O) or may bear an -oxo (=O) substituent group. Said heterocycloalkyl (i.e. heterocyclic radical or group) may be further optionally substituted on the available positions in the ring, namely on a carbon atom, or on an heteroatom available for substitution. Substitution on a carbon atom includes spiro disubstitution as well as substitution on two adjacent carbon atoms, in both cases thus form additional condensed 5 to 6 membered heterocyclic ring. Examples of $(C_3-C_6)$ heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, dihydroisoxazolyl, pyrrolidin-2-one-yl, dihydropyrrolyl radicals and the like.

Specific examples of said heterocycle radicals are 1-pyrrolidinyl, 1-methyl-2-pyrrolidinyl, 1-piperidinyl, 1-piperazinyl, 4-morpholinyl, piperazin-4-yl-2-one, 4-methylpiperazine-1-yl, 1-methylpiperidin-4-yl, 4-metylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, and (3aR,6aS)-5-methyl-octahydropyrrolo[3,4-c]pyrrol-2-yl.

The term "aryl $(C_1-C_6)$ alkyl" refers to an aryl ring linked to a straight-chained or branched alkyl groups wherein the number of carbon atoms is from 1 to 6, e.g. phenylmethyl (i.e. benzyl), phenylethyl or phenylpropyl.

Likewise the term "heteroaryl $(C_1-C_6)$ alkyl" refers to an heteroaryl ring linked to a straight-chained or branched alkyl groups wherein the number of carbon atoms is from 1 to 6, e.g. furanylmethyl.

The term "alkanoyl", refers to HC(O)— or to alkylcarbonyl groups (e.g. $(C_1-C_6)$alkylC(O)— wherein the group "alkyl" has the meaning above defined. Examples include formyl, acetyl, propanoyl, butanoyl.

Likewise "$(C_1-C_6)$alkyl-sulfonyl" refers to a "$(C_1-C_6)$ alkyl-S(O)$_2$ group wherein alkyl has the meaning above defined. An example is represented by methylsulfonyl.

The term "carbamoyl" refers to amino carbonyl derived groups —C(O)NR$_7$R$_8$, wherein R$_7$ and R$_8$ are as defined above in the definition of aminoalkyl groups and including substituted (preferred aminoalkyl substituted) and spiro substituted derivatives. Examples of such carbamoyl groups include aminocarbonyl, piperazine-1-carbonyl, morpholine-N-carbonyl, morpholine-N-carbonyl, N-(2-(dimethylamino)ethyl)aminocarbonyl, N-(2-(dimethylamino)ethyl)-N-methylaminocarbonyl, N-(3-(dimethylamino)propyl)-N-methylaminocarbonyl, 4-methylpiperazine-1-carbonyl, 4-(dimethylamino)piperidin-1-carbonyl, N-(2-(4-methylpiperazin-1-yl)ethyl)aminocarbonyl, (2-morpholino-ethyl) aminocarbonyl, N-methyl-N-(2-morpholino-ethyl)aminocarbonyl, N-(2-(piperidin-1-yl)ethyl)aminocarbonyl, N-methyl-N-(2-(piperidin-1-yl)ethyl)aminocarbonyl, N-(1-methylpiperidin-4-yl-methyl) aminocarbonyl, N-methyl-N-(1-methylpiperidin-4-yl)aminocarbonyl, N-methyl-N-(1-methylpiperidin-4-yl)aminocarbonyl, 5-methyloctahydropyrrolo[3,4-c]pyrrole-2 carbonyl.

The term "hydroxycarbonyl" refers to a terminal group HOC(O)—.

The term "$(C_1-C_{10})$ alkoxy" or "$(C_1-C_{10})$ alkoxyl", likewise "$(C_1-C_6)$ alkoxy" or "$(C_1-C_6)$ alkoxyl" etc., refers to a straight or branched hydrocarbon of the indicated number of carbons, linked to the rest of the molecule through an oxygen bridge. Likewise "$(C_1-C_6)$alkylthio" refers to the above hydrocarbon linked through a sulfur bridge.

The expression "$(C_1-C_6)$ haloalkoxy" or "$(C_1-C_6)$ haloalkoxyl" refers to the above defined haloalkyl, linked through an oxygen bridge, e.g. trifluoromethoxy.

By analogy, the expressions "$(C_3-C_6)$ heterocycloalkyloxyl" and "$(C_3-C_6)$ heterocycloalkyl $(C_1-C_6)$ alkoxyl" refer to heterocycloalkyl groups linked through an oxygen bridge and chained heterocycloalkyl-alkoxyl groups respectively. Examples of such $(C_3-C_6)$ heterocycloalkyloxyl and $(C_3-C_6)$ heterocycloalkyl $(C_1-C_6)$ alkoxyl groups are respectively (piperidin-4-yl)oxy, 1-methylpiperidin-4-yl)oxy, 2-(piperidin-4-yl)ethoxyl, 2-(1-methylpiperidin-4-yl)ethoxy, and 2-(4-morpholino)ethoxy.

The expressions "Aryloxyl" and "Aryl $(C_1-C_6)$ alkoxyl" likewise "heteroAryloxyl" and "Heteroaryl $(C_1-C_6)$ alkoxyl" refer to Aryl or Heteroaryl groups linked through an oxygen bridge and chained Aryl-alkoxyl or HeteroAryl-alkoxyl groups. Examples of such groups are phenyloxy, benzyloxy and pyridinyloxy respectively.

Likewise, the expressions "($C_3$-$C_6$) heterocycloalkyl-($C_1$-$C_6$) alkyl" and "($C_3$-$C_6$) cycloalkyl-($C_1$-$C_6$) alkyl" refer to the above defined heterocycloalkyl and cycloalkyl groups linked to the rest of the molecule via an alkyl group of the indicated number of carbons. Examples include piperidin-4-yl-methyl and cyclohexylethyl.

The expression "($C_1$-$C_6$) alkoxy-($C_1$-$C_6$) alkyl" refers to the above defined alkoxy group linked to the rest of the molecule via an alkyl group of the indicated number of carbons. Examples include methoxymethyl and methoxypropyl.

The expression "($C_1$-$C_6$) alkoxycarbonyl" refers to the above defined alkoxy group linked to the rest of the molecule via a carbonyl group, e.g. ethoxycarbonyl.

The expression like "($C_1$-$C_6$) alkoxycarbonyl-amino" refers to the above defined alkoxy group linked to the rest of the molecule via a carbonyl group followed by an amino group (—$NR_7$—), e.g. tert-butoxy-carbonyl-amino-.

"($C_1$-$C_6$) alkoxycarbonyl ($C_3$-$C_6$) heterocycloalkyl ($C_1$-$C_6$) alkyl" refers to alkoxy carbonyl heterocycloalkyl substituents enchained in said order and linked to the rest of the molecule via an alkyl group of the indicated number of carbons, e.g. (tert-butyl piperidine-1-carboxylate)-4 yl-methyl.

The expression "($C_1$-$C_6$) aminoalkoxyl" refers to ($C_1$-$C_6$) aminoalkyl groups as defined above linked through an oxygen bridge, e.g. (2-(dimethylamino)ethoxy.

The expression "($C_1$-$C_6$) hydroxyalkoxyl" refers to hydroxyalkyl groups as defined above linked to the rest of the molecule through an oxygen bridge, e.g. hydroxyethoxy.

The expression "($C_1$-$C_6$) aminoalkylcarbamoyl" refers to a "carbamoyl" group, as defined above, substituted with a ($C_1$-$C_6$) aminoalkyl group (i.e. —C(O)$NR_7R_8$ wherein e.g. $R_8$ is an ($C_1$-$C_6$) aminoalkyl), e.g. 2(dimethylamino) ethyl carbamoyl.

The term "aryl oxyl ($C_1$-$C_6$) alkyl" refers to an aryl-O— wherein aryl has the meaning above defined linked to the rest of the molecule via an alkyl group of the indicated number of carbons, e.g. phenoxyethyl.

The term "aryl alkanoyl" refers to an arylC(O) or arylalkylcarbonyl group [e.g. Aryl($C_1$-$C_6$)alkylC(O)—] wherein aryl and alkyl have the meaning above defined. Examples are represented by benzoyl, phenylacetyl, phenylpropanoyl or phenylbutanoyl radicals. Likewise "aryl sulfonyl"" refers to an aryS(O)$_2$ group wherein aryl has the meaning above defined, e.g. phenylsulfonyl.

Likewise, enchained substituents derive their definition from the composing fragments, like in the above reported definitions, such as "($C_3$-$C_6$) cycloalkyl-carbonyl", "($C_3$-$C_6$) heterocycloalkyl-carbonyl", "heteroaryl-carbonyl"; referring to the above defined fragments linked to the rest of the molecule via a carbonyl group. Examples of such groups include cyclopropanecarbonyl, pyrrolidine-3-carbonyl, (pyridin-3-yl)carbonyl.

The expression "saturated, partially unsaturated or aromatic, five or six membered cycloalkane-diyl, arylene-diyl or heterocycle-diyl" refers to suitable disubstituted cycloalkane or heterocycle or aromatic residue with five or six elements including 1,2-, 1,3- or 1,4-benzene-diyl; 2,3-, 3,4-, 4,5- or 5,6-pyridine-diyl; 3,4-, 4,5- or 5,6-pyridazine-diyl; 4,5- or 5,6-pyrimidine-diyl; 2,3-pyrazinediyl; 2,3-, 3,4- or 4,5-thiophene-diyl/furane-diyl/pyrrole-diyl; 4,5-imidazole-diyl/oxazole-diyl/thiazolediyl; 3,4- or 4,5-pyrazole-diyl/isoxazolediyl/isothiazole-diyl their saturated or partially unsaturated analogues and the like. Other non-vicinal disubstituted residues (diradical) are included too, such as 4,6-pyrimidine-diyl, and the like.

The expression "ring system" refers to mono- or bicyclic or polycyclic ring systems which may be saturated, partially unsaturated or unsaturated, such as aryl, ($C_3$-$C_{10}$) cycloalkyl, ($C_3$-$C_6$)heterocycloalkyl or heteroaryl.

The terms "group", "radical" or "fragment" or "substituent" are synonymous and are intended to indicate functional groups or fragments of molecules attachable to a bond or other fragments or molecules. Thus, as an example, a "heterocyclic radical" herein refers to a mono- or bi-cyclic saturated or partially saturated heterocyclic moiety (group, radical), preferably a 4 to 11 membered monocyclic radical, at least one further ring carbon atom in said heterocyclic radical is optionally replaced by at least one further heteroatom independently selected from N, S or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring. Examples of said heterocycle radicals are 1-pyrrolidinyl, 1-piperidinyl, 1-piperazinyl, 4-morpholinyl, piperazin-4-yl-2-one, 4-methylpiperazine-1-yl, 4-metylpiperazine-1-yl-2-one, 7-methyl-2,7-diazaspiro-[3.5]nonan-2-yl, 2-methyl-2,9-diazaspiro[5.5]undecan-9-yl, 9-methyl-3,9-diazaspiro[5.5]-undecan-3-yl, and (3aR,6aS)-5-methyl-octahydropyrrolo[3,4-c]pyrrol-2-yl and the like.

A dash ("-") that is not between two letters or symbols is meant to represent the point of attachment for a substituent. When graphically represented the point of attachment in a cyclic functional group is indicated with a dot ("•") localized in one of the available ring atom where the functional group is attachable to a bond or other fragment of molecules.

An oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—. In general, the bracketed group is a lateral group, not included into the chain, and brackets are used, when deemed useful, to help disambiguating linear chemical formulas; e.g. the sulfonyl group —$SO_2$— might be also represented as —$S(O)_2$— to disambiguate e.g. with respect to the sulfinic group —S(O)O—.

When a numerical index is used like in the statement "p is zero or an integer from 1 to 3" the statement (value) "p is zero" means that the substituent R is absent, that is to say there is no substituent R on the ring.

Whenever basic amino or quaternary ammonium groups are present in the compounds of formula I, physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups such as COOH groups, corresponding physiological cation salts may be present as well, for instance including alkaline or alkaline earth metal ions.

It will be apparent that compounds of formula (I) when contain one or more stereogenic center, may exist as optical stereoisomers.

Where the compounds of the invention have at least one stereogenic center, they may accordingly exist as enantiomers. Where the compounds according to the invention possess two or more stereogenic centers, they may additionally exist as diastereoisomers. All such single enantiomers, diastereoisomers and mixtures thereof in any proportion are encompassed within the scope of the invention. The absolute configuration (R) or (S) for carbon bearing a stereogenic center is assigned on the basis of Cahn-Ingold-Prelog nomenclature rules based on groups' priorities.

The invention further concerns the corresponding deuterated derivatives of compounds of formula (I).

All preferred groups or embodiments described above and herebelow for compounds of formula I may be combined among each other and apply as well mutatis mutandis.

In a preferred embodiment, the invention is directed to compounds of formula (I) as defined above:

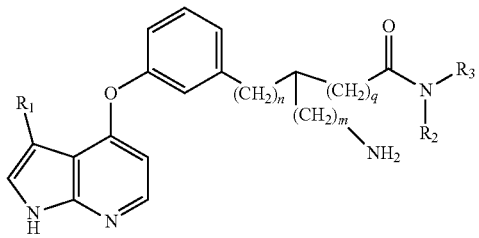

(I)

wherein
n, q and m are zero or 1;
$R_1$ is ($C_1$-$C_6$) alkyl,
$R_2$ and $R_3$, the same or different, are selected from the group consisting of
—H,
($C_1$-$C_6$) aminoalkyl,
($C_1$-$C_6$) alkoxy ($C_1$-$C_6$) alkyl,
heteroaryl($C_1$-$C_6$)alkyl,
or alternatively,
$R_2$ and $R_3$, taken together with the nitrogen atom they are linked to, form a mono-cyclic saturated or partially saturated heterocyclic radical, wherein at least one further ring carbon atom in said heterocyclic radical is optionally replaced by N,
said heterocyclic radical being optionally in its turn further substituted with one or more ($C_1$-$C_6$) alkyl groups.

In a second preferred embodiment, the invention is directed to compounds of formula (I) as defined above:

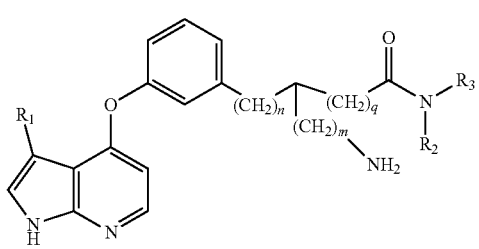

(I)

wherein n, q and m are zero or 1;
$R_1$ is methyl,
$R_2$ and $R_3$, the same or different, are selected from the group consisting of:
—H,
dimethylaminopropyl,
methoxypropyl,
pyridinylethyl;
or alternatively,
$R_2$ and $R_3$, taken together with the nitrogen atom they are linked to, form a mono-cyclic 6-membered saturated or partially saturated heterocyclic radical, wherein at least one further ring carbon atom in said heterocyclic radical is optionally replaced by N,
said heterocyclic radical being optionally in its turn further substituted with one or more methyl groups.

In a third preferred embodiment, the invention is directed to compounds of formula (I) as defined above:

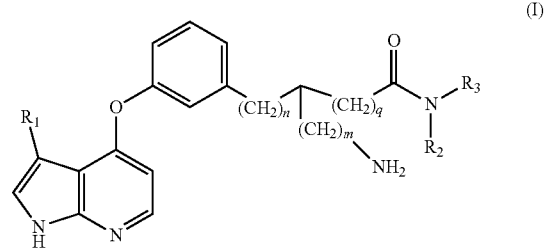

(I)

wherein
n, q and m are zero or 1;
$R_1$ is methyl,
$R_2$ and $R_3$, the same or different, are selected from the group consisting of:
—H,
methoxypropyl,
pyridinylethyl;
or alternatively,
$R_2$ and $R_3$, taken together with the nitrogen atom they are linked to, form a mono-cyclic 6-membered saturated or partially saturated heterocyclic radical, wherein at least one further ring carbon atom in said heterocyclic radical is optionally replaced by N, substituted with one methyl group.

The invention also provides a pharmaceutical composition comprising a compound of formula I, or a pharmaceutically acceptable salt thereof in admixture with one or more pharmaceutically acceptable carrier or excipient, either alone or in combination with one or more further active ingredient.

In one aspect, the invention provides a compound of formula (I) for use as a medicament.

In a further aspect, the invention provides the use of a compound of formula (I), or a pharmaceutically acceptable salt thereof, in the manufacture of a medicament for the treatment of disorders associated with ROCK enzymes mechanisms, particularly for the treatment of disorders such as pulmonary diseases.

In particular, the invention provides compounds of formula (I) for use in the prevention and/or treatment of pulmonary disease selected from the group consisting of asthma, chronic obstructive pulmonary disease COPD, idiopathic pulmonary fibrosis (IPF), pulmonary hypertension (PH) and specifically Pulmonary Arterial Hypertension (PAH).

The invention also provides a method for the prevention and/or treatment of disorders associated with ROCK enzymes mechanisms, said method comprising administering to a patient in need of such treatment a therapeutically effective amount of a compound of the invention.

In particular the invention provides methods for the prevention and/or treatment wherein the disorder is asthma, chronic obstructive pulmonary disease COPD idiopathic pulmonary fibrosis (IPF), Pulmonary hypertension (PH) and specifically Pulmonary Arterial Hypertension (PAH).

According to specific embodiments, the invention provides the compounds listed in the table below and pharmaceutical acceptable salts thereof.

| Ex. N. | Chemical Name |
|---|---|
| 1 | 2-amino-3-(3-((3-methyl-1H-pyrrolo[2,3-b]pyridin-4-yl)oxy)phenyl)-1-(4-methylpiperazin-1-yl)propan-1-one |
| 2 | 2-amino-N-(3-methoxypropyl)-3-(3-((3-methyl-1H-pyrrolo[2,3-b]pyridin-4-yl)oxy)phenyl)propanamide |
| 3 | 2-amino-N-(3-(dimethylamino)propyl)-3-(3-((3-methyl-1H-pyrrolo[2,3-b]pyridin-4-yl)oxy)phenyl)propanamide |
| 4 | 2-amino-3-(3-((3-methyl-1H-pyrrolo[2,3-b]pyridin-4-yl)oxy)phenyl)-N-(2-(pyridin-4-yl)ethyl)propanamide |
| 5 | 3-amino-3-(3-((3-methyl-1H-pyrrolo[2,3-b]pyridin-4-yl)oxy)phenyl)-1-(4-methylpiperazin-1-yl)propan-1-one |
| 6 | 3-amino-N-(3-methoxypropyl)-3-(3-((3-methyl-1H-pyrrolo[2,3-b]pyridin-4-yl)oxy)phenyl)propanamide |
| 7 | 3-amino-3-(3-((3-methyl-1H-pyrrolo[2,3-b]pyridin-4-yl)oxy)phenyl)-N-(2-(pyridin-4-yl)ethyl)propanamide |
| 8 | 3-amino-N-(3-(dimethylamino)propyl)-3-(3-((3-methyl-1H-pyrrolo[2,3-b]pyridin-4-yl)oxy)phenyl)propanamide |
| 9 | 3-amino-2-(3-((3-methyl-1H-pyrrolo[2,3-b]pyridin-4-yl)oxy)benzyl)-1-(4-methylpiperazin-1-yl)propan-1-one |
| 10 | 3-amino-N-(3-methoxypropyl)-2-(3-((3-methyl-1H-pyrrolo[2,3-b]pyridin-4-yl)oxy)benzyl)propanamide |
| 11 | 3-amino-2-(3-((3-methyl-1H-pyrrolo[2,3-b]pyridin-4-yl)oxy)benzyl)-N-(2-(pyridin-4-yl)ethyl)propanamide |
| 12 | 3-amino-N-(3-(dimethylamino)propyl)-2-(3-((3-methyl-1H-pyrrolo[2,3-b]pyridin-4-yl)oxy)benzyl)propanamide |
| 13 | 4-amino-3-(3-((3-methyl-1H-pyrrolo[2,3-b]pyridin-4-yl)oxy)phenyl)-N-(2-(pyridin-4-yl)ethyl)butanamide |
| 14 | 4-amino-N-(3-methoxypropyl)-3-(3-((3-methyl-1H-pyrrolo[2,3-b]pyridin-4-yl)oxy)phenyl)butanamide |
| 15 | 4-amino-N-(3-(dimethylamino)propyl)-3-(3-((3-methyl-1H-pyrrolo[2,3-b]pyridin-4-yl)oxy)phenyl)butanamide |
| 16 | 4-amino-3-(3-((3-methyl-1H-pyrrolo[2,3-b]pyridin-4-yl)oxy)phenyl)-1-(4-methylpiperazin-1-yl)butan-1-one |

The compounds of the invention, including all the compounds hereabove listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be obtained using the processes described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

Thus, processes described below and reported in the following schemes should not be viewed as limiting the scope of the synthetic processes available for the preparation of the compounds of the invention.

In some cases, generally known protective groups (PG) could be employed when needed to mask or protect sensitive or reactive moieties, in accordance to general principles of chemistry (Protective group in organic syntheses, 3rd ed. T. W. Greene, P. G. M. Wuts).

The compounds of formula I, including all the compounds here above listed, can be generally prepared according to the procedures shown in the schemes below. Where a specific synthetic step differs from what is described in the general schemes, it has been detailed in the specific examples and/or in additional schemes.

Compounds of formula I (wherein n, q and m are zero or 1) contain at least one stereogenic centre, as marked by an asterisk * in the picture below.

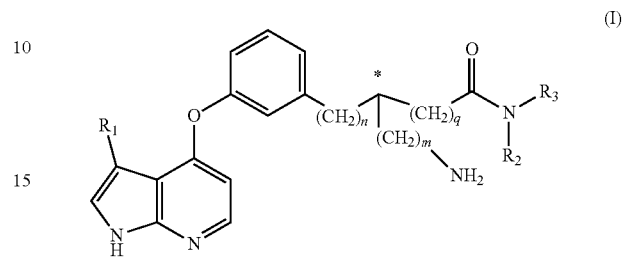

(I)

Enantiomerically pure compounds can be prepared according to the reactions described below, by means of enantiomerically pure starting materials and intermediates. Preparation of enantiomerically pure compounds of formula I may be accomplished by means for example of enantiomerically pure intermediates IV and/or VII as found in the following schemes. These intermediates may be commercially available or readily prepared from commercial sources by those of ordinary skill in the art.

In another approach, enantiomerically pure compounds can be obtained from the corresponding racemates by means of chiral chromatography. Whenever, in compounds of formula I, there are two or more stereogenic centres, the structure is then characterized by different stereoisomers. Stereochemically pure compounds may be obtained by chiral separation from a diastereoisomeric mixture, or stepwise by chromatographic separation of diastereoisomers followed by further chiral separation into single stereoisomers.

Compounds of formula I (wherein n, q and m are zero or 1) may be prepared according to SCHEME 1 as described hereinafter. SCHEME 1 also provides at least one non-limiting synthetic route for the preparation of examples 1 to 12.

Typical protective groups (PG1) for protection of the NH of the 5-membered ring of the bicyclic intermediate III can be 2-[(trimethylsilyl)ethoxy]methyl (SEM), 4-toluenesulfonyl (Ts) and p-methoxybenzyl (PMB), and anyhow not limiting the use of other protective groups. Intermediate III, wherein PG1 is SEM may be prepared from the corresponding intermediate II and a suitable reagent such as SEM-Cl ([2-(trimethylsilyl)ethoxy]methyl chloride). Reaction between said components may be carried out in a polar organic solvent such as DMF or DCM, in the presence of a strong base, such as NaH, at RT or lower.

The amino group of intermediate IV may be suitably protected as a carbamate with PG2 (for example a Boc group) and the carboxylic acid as an ester with PG3 (for example as the methyl ester or ethyl ester). These transformations may be achieved by using generally well know methods starting from commercially available unprotected amino acid derivatives (Protective group in organic syntheses, 3rd ed. T. W. Greene, P. G. M. Wuts).

According to SCHEME 1, intermediate V may be obtained from Intermediates III and IV through a palladium catalyzed O-arylation. For example, the reaction may be carried out by reacting the aryl halide intermediate III and the phenol derivative IV in a suitable organic solvent such as toluene or THF, in the presence of an inorganic base such as $K_2CO_3$, with a suitable palladium catalytic system such as $Pd_2dba_3$/XPhos or another palladium source/phosphine based ligand at high temperature (around 100° C.) for a few hours (3-6 hours).

Removal of PG3 (when PG3 is a methyl or ethyl) from intermediate V to give the intermediate VI, may be carried out by hydrolysis using an inorganic base such as LiOH in a mixture of organic solvent such as THF or methanol and water, generally at RT and for a time ranging from 10 min to overnight.

Intermediate VIII may be obtained from intermediates VI and VII through an amide coupling reaction. For example, the reaction may be performed by reacting intermediate VI and VII in the presence of an activating agent such as COMU or HATU, with an organic base such as DIPEA or TEA, in a suitable organic solvent such as DCM or DMF and at temperature generally around RT for a time ranging from a few hours to overnight. Removal of all protective groups from intermediate VIII (PG1 and PG2) to give compounds of formula I may be achieved using generally known methods (Protective group in organic syntheses, 3rd ed. T. W. Greene, P. G. M. Wuts). For example, when PG1 is SEM and PG2 is a Boc groups, cleavage may be achieved by an acidic treatment using TFA in an organic solvent such as DCM or inorganic acids in organic solvents such as hydrochloric acid in dioxane. Complete removal of SEM group may require an extra treatment with a solution of ammonia in methanol or aqueous NaOH or LiOH.

SCHEME I

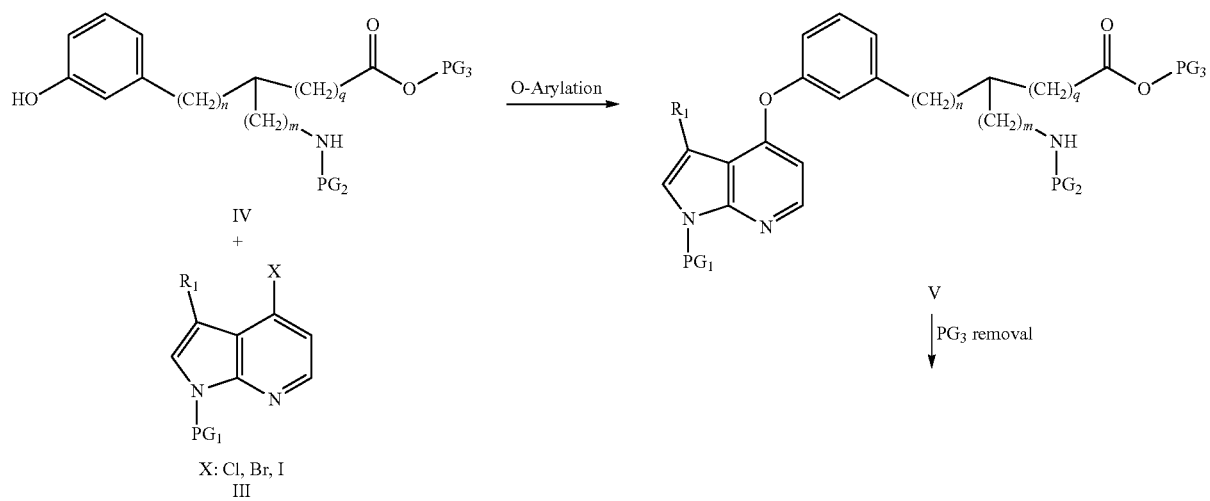

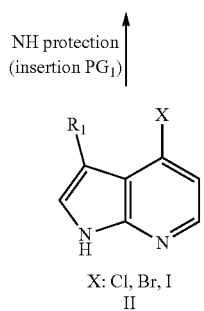

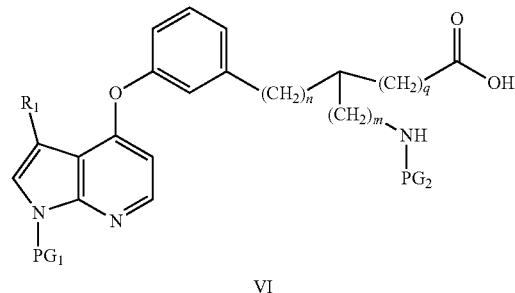

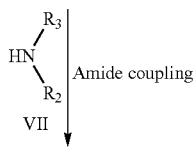

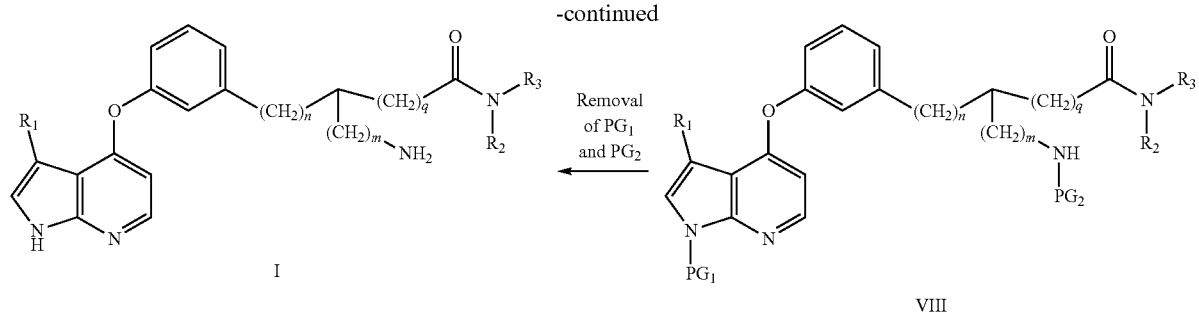
In another approach, compounds of formula I wherein n is 0, m is 1 and q is 1, may be prepared according to SCHEME 2 that also provides at least one non-limiting synthetic route for the preparation of examples 13 to 16.
SCHEME 2
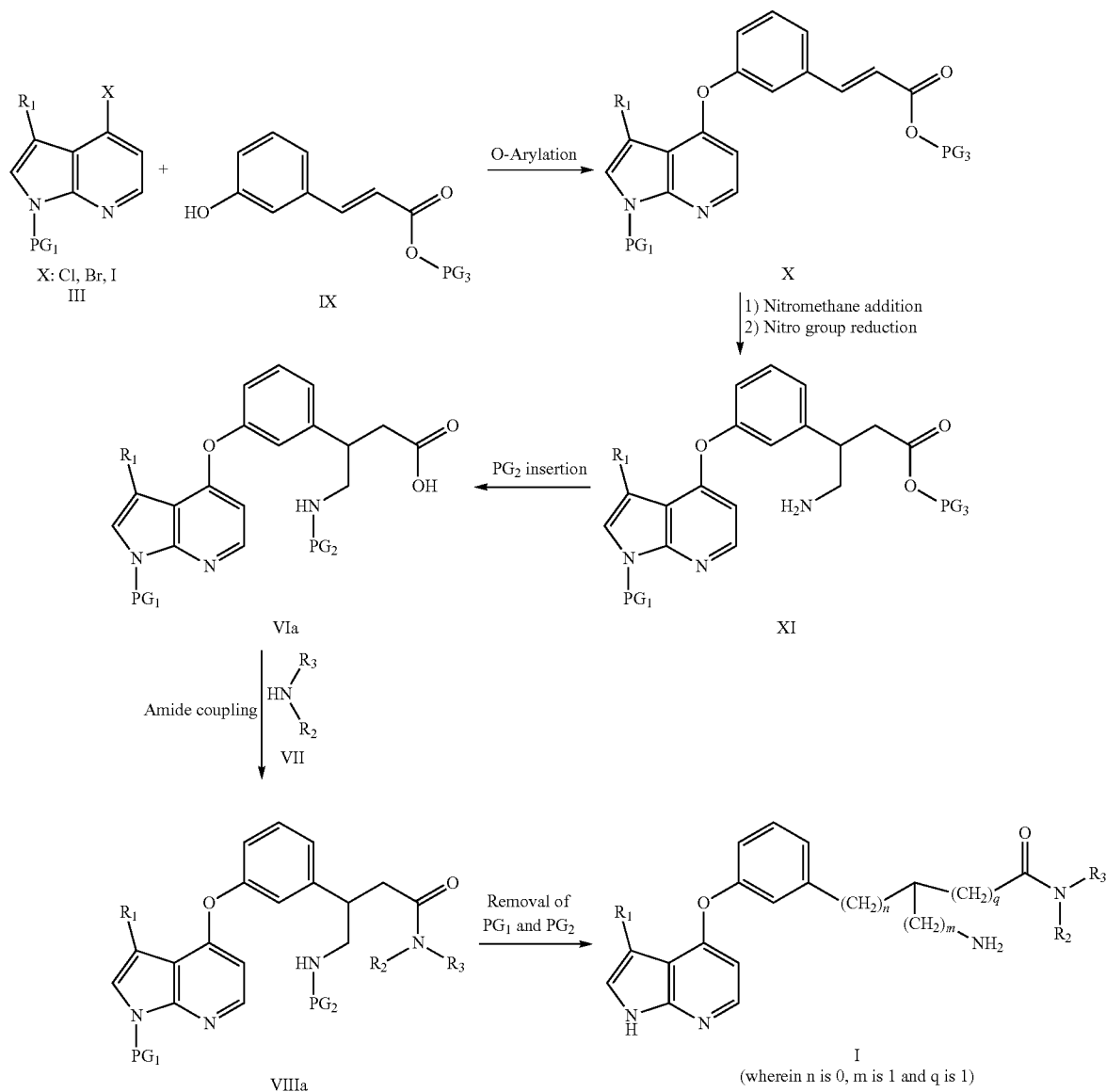

Intermediate X may be obtained from III and IX through a palladium catalyzed O-arylation. The reaction may be performed in the same way as described in SCHEME 1 for preparation of intermediate V from III and IV. Intermediate XI may be obtained from intermediate X in a two-step synthesis that requires first the 1,4-addition of nitromethane to alpha-beta unsaturated intermediate X and then reduction of the nitro group to amino. The first step may be carried out by reacting intermediate X with nitromethane used as solvent (excess) in the presence of a strong organic base such as DBU at a temperature between 0° C. and RT for a time ranging from 5 to 6 hours. In step two, the reduction of nitro group could be performed by nickel borohydride mediated reduction to give intermediate XI. For example, such a reaction may be performed by reacting the nitro intermediate with sodium borohydride in the presence of nickel (II) chloride in methanol, at a temperature between 0° C. and RT, and for a time ranging from 1-3 hours. Insertion of PG2 on the amino moiety of intermediate XI to give intermediate VIa, when PG2 is Boc, may be performed by reacting XI with tert-butyl dicarbonate in an organic solvent such as DCM or THF, in the presence of an organic base such as TEA or DIPEA, at a temperature between 0° C. and RT, for a time up to one hour.

Intermediate VIIIa may be obtained from intermediate VIa and VII in the same way as described in SCHEME 1 for intermediate the preparation of VIII from VI and VII. Compound of formula I, wherein n is 0, m is 1 and q is 1, may be obtained from intermediate VIIIa by removal of PG1 and PG2 in the same way as described in SCHEME 1 for intermediate VIII to give compound of formula I.

The compounds of the invention are inhibitors of kinase activity, in particular Rho-kinase activity. Generally speaking, compounds which are ROCK inhibitors may be useful in the treatment of many disorders associated with ROCK enzymes mechanisms.

In one embodiment, the disorders that can be treated by the compounds of the present invention include glaucoma, inflammatory bowel disease (IBD) and pulmonary diseases selected from asthma, chronic obstructive pulmonary disease (COPD), interstitial lung disease such as idiopathic pulmonary fibrosis (IPF) and pulmonary arterial hypertension (PAH).

In another embodiment, the disorder that can be treated by the compounds of the present invention is selected from the group consisting of asthma, chronic obstructive pulmonary disease (COPD) and interstitial lung disease such as idiopathic pulmonary fibrosis (IPF) and pulmonary arterial hypertension (PAH).

In a further embodiment, the disorder is selected from idiopathic pulmonary fibrosis (IPF) and pulmonary arterial hypertension (PAH).

The methods of treatment of the invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once daily or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination (i.e. as co-therapeutic agents administered in fixed dose combination or in combined therapy of separately formulated active ingredients) with other pharmaceutical active ingredients selected from organic nitrates and NO donors; inhaled NO; stimulator of soluble guanylate cyclase (sGC); prostacyclin analogue PGI2 and agonist of prostacyclin receptors; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors; human neutrophilic elastase inhibitors; compounds inhibiting the signal transduction cascade, such as tyrosine kinase and/or serine/threonine kinase inhibitors; antithrombotic agents, for example platelet aggregation inhibitors, anticoagulants or profibrinolytic substances; active substances for lowering blood pressure, for example calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists; neutral endopeptidase inhibitor; osmotic agents; ENaC blockers; anti-inflammatory including corticosteroids and antagonists of chemokine receptors; bronchodilators for example beta2agonist and muscarinic antagonists; antihistamine drugs; anti-tussive drugs; antibiotics such as macrolide and DNase drug substance and selective cleavage agents such as recombinant human deoxyribonuclease I (rhDNase); agents that inhibit ALK5 and/or ALK4 phosphorylation of Smad2 and Smad3; tryptophan hydroylase 1 (TPH1) inhibitors and multi-kinase inhibitors.

In a preferred embodiment, the compounds of the invention are dosed in combination with phosphodiesterase V such as sildenafil, vardenafil and tadalafil; organic nitrates and NO donors (for example sodium nitroprusside, nitroglycerin, isosorbide mononitrate, isosorbide dinitrate, molsidomine or SIN-1, and inhaled NO); synthetic prostaciclin analogue PGI2 such as iloprost, treprostinil, epoprostenol and beraprost; agonist of prostacyclin receptors such as selexipag and compounds of WO 2012/007539; stimulator of soluble guanylate cyclase (sGC) like riociguat and tyrosine kinase like imatinib, sorafenib and nilotinib and endothelin antagonist (for example macitentan, bosentan, sitaxentan and ambrisentan).

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage comprised between 0.001 and 1000 mg/day, preferably between 0.1 and 500 mg/day.

When the compounds of formula (I) are administered by inhalation route, they are preferably given at a dosage comprised between 0.001 and 500 mg/day, preferably between 0.1 and 100 mg/day.

A pharmaceutical composition comprising a compound of the invention suitable to be administered by inhalation, such as inhalable powders, propellant-containing metering aerosols or propellant-free inhalable formulations.

The invention is also directed to a device comprising the pharmaceutical composition comprising a compound according to the invention, which may be a single- or multi-dose dry powder inhaler, a metered dose inhaler and a soft mist nebulizer.

The following examples illustrate the invention.

PREPARATIONS OF INTERMEDIATES AND EXAMPLES

General Experimental Details

Purification by chromatography refers to purification using the CombiFlash® Companion purification system/Teledyne Isco RF 200 purification system or the Biotage SP1 purification system. Si cartridge refers to an Isolute® SPE Si II cartridge, a pre-packed polypropylene column containing unbonded activated silica with irregular particles with average size of 50 μm and nominal 60 Å porosity. Fractions containing the required product (identified by TLC and/or LCMS analysis) were pooled and concentrated in vacuo. Where an SCX-2 cartridge was used, 'SCX-2 cartridge' refers to an Isolute® pre-packed polypropylene column containing a non-end-capped propylsulphonic acid functionalised silica strong cation exchange sorbent. Where HPLC was used for purification (Purification by MDAP) fractions containing the required product (identified by TLC and/or LCMS analysis) were pooled and the solvent removed using a Biotage EV10 Evaporator. Alternatively the pooled product fraction was lyophilised.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz or on a Bruker Fourier 300 spectrometer with a 5 mm dual probe operating at 300 MHz. Shifts are given in ppm relative to tetramethylsilane.

LC-MS Method 1

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid.

Gradient:

| Gradient – Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 2

Waters Micromass ZQ2000 mass spectrometer with a C18-reverse-phase column (100×2.1 mm Acquity BEH with 1.7 µm particle size) maintained at 40° C., elution with A: water+0.1% aqueous ammonia; B: MeCN+0.1% aqueous ammonia.

Gradient:

| Gradient – Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 3

Quattro Micro Mass Spectrometer with a C18-reverse-phase column (100×2.1 mm Acquity BEH with 1.7 µm particle size) maintained at 40° C., elution with A: water+0.1% formic acid; B: MeCN+0.1% formic acid.

Gradient:

| Gradient – Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 4

QDa Mass Spectrometer with a C18-reverse-phase column (50×2.1 mm Acquity CSH with 1.7 µm particle size) maintained at 40° C., elution with A: water+0.1% formic acid; B: MeCN+0.1% formic acid.

Gradient:

| Gradient – Time | flow (mL/min) | % A | % B |
| --- | --- | --- | --- |
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionisation method-Electrospray (positive/negative ion).

LC-MS Method 5

QDa Mass Spectrometer with a C18-reverse-phase column (50×2.1 mm Acquity BEH with 1.7 µm particle size) maintained at 50° C., elution with A: water+0.1% formic acid; B: MeCN+0.1% formic acid.

Gradient:

| Gradient – Time | flow (mL/min) | % A | % B |
| --- | --- | --- | --- |
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionisation method-Electrospray (positive/negative ion).

MDAP Method

Agilent Technologies 1260 Infinity purification system with an XBridge Prep C18 OBD column (19×250 mm, 5 µm OBD) maintained at RT Mobile Phase A: 0.1% aqueous ammonia Mobile Phase B: 0.1% ammonia in acetonitrile Flow Rate: 20 ml/min Gradient Program: 10%-95%, 22 min, centered around a specific focused gradient Sample: Injection of a 20-60 mg/ml solution in DMSO+ optional formic acid and water)

Abbreviations Used in the Experimental Section:

COMU=(1-Cyano-2-ethoxy-2-oxoethylidenaminooxy)dimethylaminomorpholino-carbenium hexafluorophosphate; DBU=1,8-Diazabicyclo[5.4.0]undec-7-ene; DCM=Dichloromethane; DIPEA=Di-isopropylethylamine; DMF=N,N-dimethylformamide; DMSO=Dimethylsulphoxide; h=Hour(s); LCMS=Liquid chromatography-mass spectrometry; min=Minute(s); MDAP=Mass-directed autopurification; Pd$_2$(dba)$_3$=Tris (dibenzylideneacetone)dipalladium(O); Rt=Retention time; RT=Room temperature; TFA=Trifluoroacetic acid; TEA=Triethylamine; THF=Tetrahydrofuran; XPhos=2-Dicyclohexylphosphino-2',4',6'-triisopropylbiphenyl.

In the procedures that follow, some of the starting materials are identified through an "Intermediate" or "Example" number with indications on step. This is provided merely for assistance to the skilled chemist.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Example 1

Step A

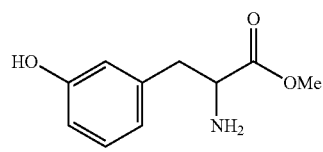 [SMILES: COC(=O)C(N)Cc1cccc(O)c1]

Methyl 2-amino-3-(3-hydroxyphenyl)propanoate (Intermediate 1A-a)

Methyl 2-amino-3-(3-hydroxyphenyl)propanoate (5.56 g, 30.76 mmol) was suspended in methanol (120 mL) and the mixture was cooled in an ice bath. Thionyl chloride (11.2 mL, 154 mmol) was added dropwise. The mixture was allowed to warm to RT and then stirred overnight. The solvent was evaporated and the residue dissolved in water (50 mL). After basifying the mixture using saturated aqueous sodium hydrogen carbonate, the product was extracted into ethyl acetate (5×50 mL). The combined organic extracts were dried (Na₂SO₄) and evaporated to give the desired product as a white solid (4.97 g).

LCMS (Method 4): Rt=0.25 min, m/z 196.1 [M+H]⁺

Step B

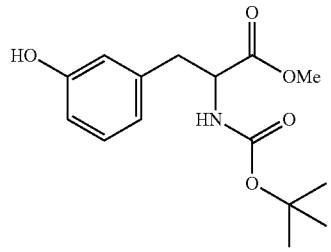 [SMILES: COC(=O)C(Cc1cccc(O)c1)NC(=O)OC(C)(C)C]

Methyl 2-((tert-butoxycarbonyl)amino)-3-(3-hydroxyphenyl)propanoate (Intermediate 1B-a)

Intermediate 1A-a (4.97 g, 25.4 mmol) was suspended in a mixture of DCM (200 mL) and THF (100 mL) and DIPEA (9.07 mL, 50.8 mmol) was added. The mixture was cooled in an ice bath and di-tert-butyl dicarbonate (6.10 g, 27.9 mmol) was added portionwise. The reaction mixture was allowed to warm to RT and stirred for 18 h. The solvent was evaporated in vacuo and the crude product was purified by chromatography on a 50 g Si cartridge eluting with 0-50% EtOAc in DCM. Intermediate 1B-a was obtained as a white solid (6.33 g).

LCMS (Method 4): Rt=1.27 min, m/z 318.1 [M+Na]⁺

Step C

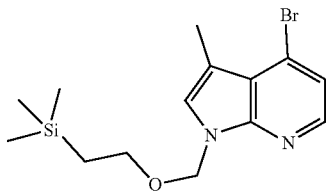 [SMILES: Cc1cn(COCC[Si](C)(C)C)c2nccc(Br)c12]

4-Bromo-3-methyl-1-((2-(trimethylsilyl)ethoxy)methyl)-1H-pyrrolo[2,3-b]pyridine (Intermediate 1C-a)

4-Bromo-3-methyl-7-azaindole (4.0 g, 18.95 mmol) was dissolved in DMF (37 mL) and the solution was cooled in an ice bath. Sodium hydride (60% on mineral oil, 1.14 g, 28.43 mmol) was added and the mixture was stirred under a stream of nitrogen for 1 h. 2-(Trimethylsilyl)ethoxymethyl chloride (4.0 mL, 22.74 mmol) was added dropwise and then the reaction mixture was stirred for a further 30 min. After quenching with water (20 mL), the product was extracted into ethyl acetate (3×20 mL). The combined extracts were dried (Na₂SO₄) and evaporated. The residue was chromatographed on a 120 g Si cartridge eluting with 0-25% ethyl acetate in cyclohexane to give Intermediate 1C-a as a colourless oil (3.78 g).

LCMS (Method 5): Rt=1.90 min, m/z 341.1/343.0 [M+H]⁺

Step D

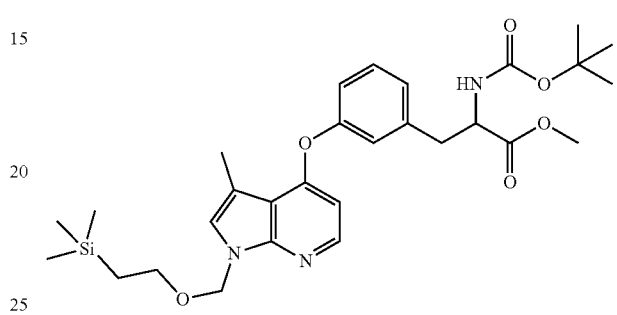

Methyl 2-((tert-butoxycarbonyl)amino)-3-(3-((3-methyl-1-((2-(trimethylsilyl)-ethoxy)methyl)-1H-pyrrolo[2,3-b]pyridin-4-yl)oxy)phenyl)propanoate (Intermediate 1D-a)

A mixture of Intermediates 1B-a (1.89 g, 6.4 mmol) and 1C-a (1.985 g, 5.8 mmol), Pd₂(dba)₃ (0.265 g, 0.29 mmol), XPhos (0.275 g, 0.58 mmol) and potassium carbonate (1.70 g, 12.3 mmol) in toluene (73 mL) was sonicated for 5 min under a blanket of argon. The mixture was heated at 100° C. for 4 h, and then allowed to cool to RT before filtering through Celite. The solvent was evaporated to give the crude product. This was purified by chromatography on a 50 g Si cartridge eluting with 10-40% ethyl acetate in cyclohexane. The material obtained was further purified twice by chromatography on a 20 g Si cartridge eluting with 10-20% ethyl acetate in DCM. The product was obtained as a viscous red/brown oil (2.65 g).

LCMS (Method 4): Rt=1.87 min, m/z 556.4 [M+H]⁺

Step E

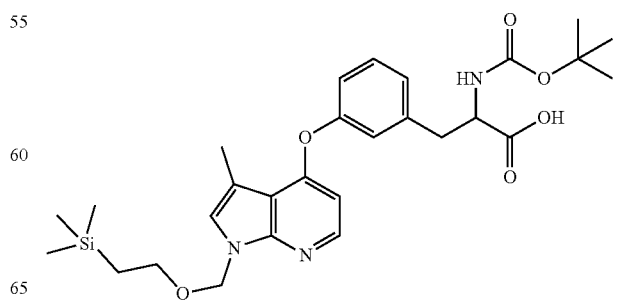

2-((tert-Butoxycarbonyl)amino)-3-(3-((3-methyl-1-((2-(trimethylsilyl)-ethoxy)methyl)-1H-pyrrolo[2,3-b]pyridin-4-yl)oxy)phenyl)propanoic acid (Intermediate 1E-a)

Intermediate 1D-a (2.65 g, 4.7 mmol) was dissolved in a mixture of methanol (23 mL), water (23 mL) and THF (11.5 mL). Lithium hydroxide monohydrate (0.59 g, 14.1 mmol) was added and the reaction mixture was stirred at RT for 10 min. The solvents were partially evaporated and the product was extracted into ethyl acetate (4×30 mL). The combined organic extracts were dried (Na$_2$SO$_4$) and evaporated to give a beige foam (2.5 g).

LCMS (Method 4): Rt=1.79 min, m/z 542.4 [M+H]$^+$

Step F

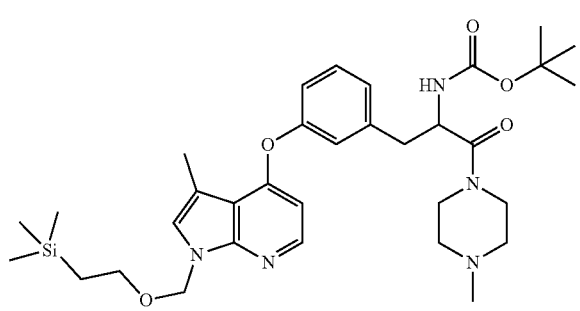 [SMILES: Cc1cn(COCC[Si](C)(C)C)c2nccc(Oc3cccc(CC(NC(=O)OC(C)(C)C)C(=O)N4CCN(C)CC4)c3)c12]

tert-Butyl (3-(3-((3-methyl-1-((2-(trimethylsilyl)ethoxy)methyl)-1H-pyrrolo[2,3-b]pyridin-4-yl)oxy)phenyl)-1-(4-methylpiperazin-1-yl)-1-oxopropan-2-yl)carbamate (Intermediate 1F-a)

Intermediate 1E-a (272 mg, 0.50 mmol), 1-methylpiperazine (0.061 mL, 0.55 mmol) and COMU (257 mg, 0.60 mmol) were dissolved in DCM (7.5 mL). DIPEA (0.142 mL, 1.10 mmol) was added and the reaction mixture was stirred at RT for 2.5 h. Then, a further amount of 1-methylpiperazine (0.0061 mL, 0.055 mmol) and COMU (26 mg, 0.06 mmol) was added. Stirring was continued for a further 2 h. Water (20 mL) was added and the DCM layer was separated. The aqueous was further extracted with DCM (2×10 mL) and the combined organic extracts were dried (Na$_2$SO$_4$) and evaporated. The product was purified by chromatography on a 5 g Si II cartridge eluting with 50% ethyl acetate in DCM then with Ethyl acetate followed by 2-8% methanol in ethyl acetate. Intermediate 1F-a was obtained as a yellow gum (270 mg).

LCMS (Method 4): Rt=1.30 min, m/z 624.5 [M+H]$^+$

Step G

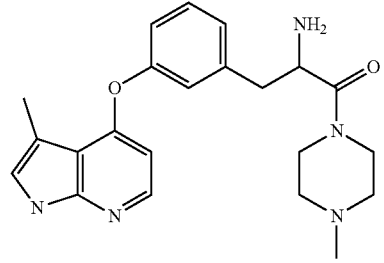 [SMILES: Cc1c[nH]c2nccc(Oc3cccc(CC(N)C(=O)N4CCN(C)CC4)c3)c12]

2-Amino-3-(3-((3-methyl-1H-pyrrolo[2,3-b]pyridin-4-yl)oxy)phenyl)-1-(4-methylpiperazin-1-yl)propan-1-one (Example 1)

Intermediate 1F-a (270 mg, 0.64 mmol) was dissolved in a mixture of DCM (2.5 mL) and TFA (7.5 mL), and the reaction mixture was stirred at RT for 2.5 h. The mixture was passed down a 5 g SCX-2 cartridge eluting with DCM, methanol and then 2M methanolic ammonia. The ammonia solution was evaporated to give a residue which was stirred with a mixture of tetrahydrofuran (5 mL) and 4M sodium hydroxide (aq) (5 mL) for 1.5h. The mix was diluted with saturated brine (15 mL) and extracted with ethyl acetate (2×15 mL). The combined organic phase was filtered through a 2 g SCX 2 cartridge. The cartridge was washed with methanol then 2M methanolic ammonia. Concentration of the ammonia fraction gave the crude product. This was purified by MDAP. Example 1 was obtained as a white solid (52 mg).

LCMS (Method 2): Rt=3.11 min, m/z 394.0 [M+H]$^+$ $^1$H NMR (400 MHz, d6-DMSO) δ 11.36 (s, 1H), 8.00 (d, J=5.4 Hz, 1H), 7.37-7.32 (m, 1H), 7.14-7.10 (m, 1H), 7.10-7.07 (m, 1H), 7.00-6.96 (m, 2H), 6.26 (d, J=5.4 Hz, 1H), 3.93 (t, J=6.8 Hz, 1H), 3.48-3.38 (m, 2H), 3.30-3.22 (m, 3H), 2.81-2.74 (m, 1H), 2.71-2.64 (m, 1H), 2.33 (d, J=1.0 Hz, 3H), 2.26-2.17 (m, 2H), 2.11 (s, 3H), 2.09-2.01 (m, 1H), 1.94-1.83 (m, 2H).

Examples 2 to 12

The following Examples were prepared in a similar way to Example 1 by replacing at each step the appropriate starting materials.

Preparation of Intermediates 1B-b and 1B-c

The following intermediates were prepared in a similar manner to Intermediate 1B-a by replacing in Step A of Example 1 the amino acid with the indicated starting materials.

| Intermediate | Structure | Starting material | LC-MS |
|---|---|---|---|
| 1B-b | ![structure] | 3-Amino-3-(3-hydroxy-phenyl)propanoic acid | Rt = 1.30 min, m/z 318.1 [M + Na]+ (Method 4) |

| Intermediate | Structure | Starting material | LC-MS |
|---|---|---|---|
| 1B-c | 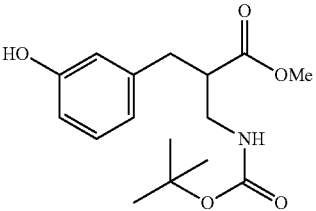 [SMILES: COC(=O)C(CNC(=O)OC(C)(C)C)Cc1cccc(O)c1] | 3-Amino-2-(3-hydroxy-benzyl)-propanoic acid (hydrochloride salt) | Rt = 1.35 min, m/z 332.1 [M + Na]+ (Method 4) |

Preparation of Intermediates from 1D-b and 1D-c

The following intermediates were prepared in a similar manner to Intermediate 1D-a from the indicated starting materials.

| Intermediate | Structure | Starting materials | LC-MS |
|---|---|---|---|
| 1D-b | 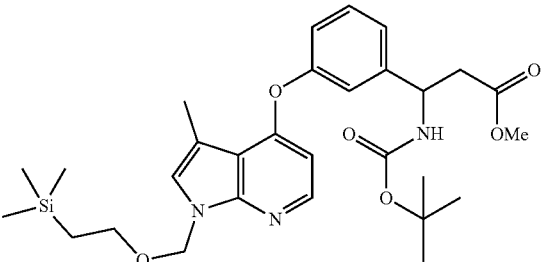 | 1B-b and 1C-a | Rt = 1.85 min, m/z 556.4 [M + H]+ (Method 4) |
| 1D-c | 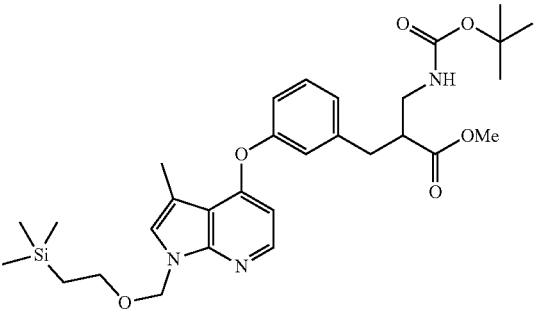 [SMILES: COC(=O)C(CNC(=O)OC(C)(C)C)Cc1cccc(Oc2ccnc3c2c(C)cn3COCC[Si](C)(C)C)c1] | 1B-c and 1C-a | Rt = 1.94 min, m/z 570.4 [M + H]+ (Method 4) |

Preparation of Intermediates from 1E-b and 1E-c

The following intermediates were prepared in a similar manner to Intermediate 1E-a from the indicated starting materials.

| Intermediate | Structure | Starting materials | LC-MS |
|---|---|---|---|
| 1E-b | 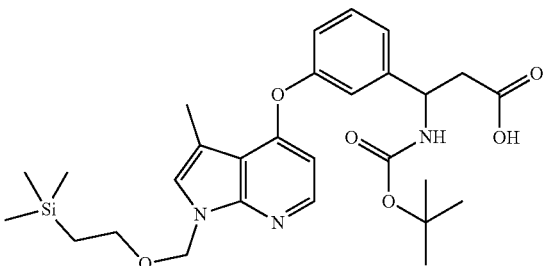 | 1D-b | Rt = 1.74 min, m/z 542.4 [M + H]+ (Method 4) |

-continued

| Intermediate | Structure | Starting materials | LC-MS |
|---|---|---|---|
| 1E-c | 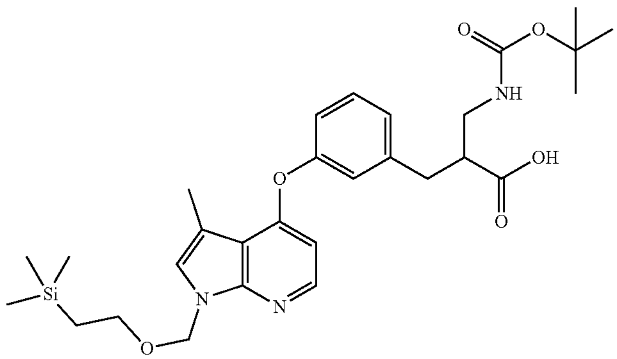 [SMILES: Cc1cn(COCC[Si](C)(C)C)c2nccc(Oc3cccc(CC(CNC(=O)OC(C)(C)C)C(=O)O)c3)c12] | 1D-c | Rt = 1.80 min, m/z 556.4 [M + H]+ (Method 4) |

Preparation of Examples 2 to 12

The following examples were prepared in a similar manner to Example 1, following the same synthetic sequence, by replacing in Step F the indicated Intermediate 1E and amine starting materials in the table below.

| Ex | Structure | Intermediate 1E/Amine | 1H NMR | LC-MS |
|---|---|---|---|---|
| 2 | 2-amino-N-(3-methoxypropyl)-3-(3-((3-methyl-1H-pyrrolo[2,3-b]pyridin-4-yl)oxy)phenyl)propanamide | 1E-a/3-methoxy-propylamine | ¹H NMR (400 MHz, d6-DMSO) δ 11.35 (s, 1H), 7.99 (d, J = 5.4 Hz, 1H), 7.82 (t, J = 5.7 Hz, 1H), 7.34 (t, J = 7.8 Hz, 1H), 7.13-7.06 (m, 2H), 7.01-6.96 (m, 2H), 6.26 (d, J = 5.4 Hz, 1H), 3.40-3.34 (m, 1H), 3.23 (t, J = 6.3 Hz, 2H), 3.18 (s, 3H), 3.09-3.01 (m, 2H), 2.88 (dd, J = 5.5, 13.3 Hz, 1H), 2.67 (dd, J = 7.6, 13.3 Hz, 1H), 2.33 (d, J = 1.0 Hz, 3H), 1.85 (s, 2H), 1.60-1.53 (m, 2H). | Rt = 2.13 min, m/z 383.4 [M + H]+ (Method 3) |
| 3 | 2-amino-N-(3-(dimethylamino)propyl)-3-(3-((3-methyl-1H-pyrrolo[2,3-b]pyridin-4-yl)oxy)phenyl)propanamide | 1E-a/3-(dimethyl-amino)-1-propyl-amine | ¹H NMR (400 MHz, d6-DMSO) δ 11.36 (s, 1H), 7.99 (d, J = 5.4 Hz, 1H), 7.83 (t, J = 5.7 Hz, 1H), 7.34 (t, J = 7.8 Hz, 1H), 7.13-7.10 (m, 1H), 7.08 (d, J = 7.4 Hz, 1H), 7.02-6.99 (m, 1H), 6.97 (dd, J = 2.5, 7.8 Hz, 1H), 6.26 (d, J = 5.4 Hz, 1H), 3.39-3.34 (m, 1H), 3.06-2.99 (m, 2H), 2.89 (dd, J = 5.5, 13.3 Hz, 1H), 2.68 (dd, J = 7.5, 13.3 Hz, 1H), 2.33 (d, J = 0.9 Hz, 3H), 2.13-2.08 (m, 2H), 2.06 (s, 6H), 1.74 (s, 2H), 1.49-1.40 (m, 2H). | Rt = 3.23 min, m/z 396.3 [M + H]+ (Method 2) |
| 4 | 2-amino-3-(3-((3-methyl-1H-pyrrolo[2,3-b]pyridin-4-yl)oxy)phenyl)-N-(2-(pyridin-4-yl)ethyl)propanamide | 1E-a/2-(4-pyridyl)-ethylamine | ¹H NMR (400 MHz, d6-DMSO) δ 11.35 (s, 1H), 8.44-8.42 (m, 2H), 7.98 (d, J = 5.4 Hz, 1H), 7.94 dd, J = 5.8, 5.8 Hz, 1H), 7.34 (dd, J = 7.9, 7.9 Hz, 1H), 7.15 (d, J = 6.0 Hz, 2H), 7.12-7.11 (m, 1H), 7.06 (d, J = 7.6 Hz, 1H), 6.99 (d, J = 7.3 Hz, 2H), 6.25 (d, J = 5.4 Hz, 1H), 3.38-3.24 (m, 3H), 2.86 dd, J = 5.3, 13.3 Hz, 1H), 2.70-2.60 (m, 3H), 2.31 (d, J = 0.8 Hz, 3H), 1.68 (s, 2H). | Rt = 3.45 min, m/z 416.5 [M + H]+ (Method 2) |

-continued

| Ex | Structure | Intermediate 1E/Amine | 1H NMR | LC-MS |
|---|---|---|---|---|
| 5 | 3-amino-3-(3-((3-methyl-1H-pyrrolo[2,3-b]pyridin-4-yl)oxy)phenyl)-1-(4-methylpiperazin-1-yl)propan-1-one | 1E-b/1-methyl piperazine | $^1$H NMR (400 MHz, d6-DMSO) δ 11.35 (s, 1H), 8.00 (d, J = 5.4 Hz, 1H), 7.37 (t, J = 7.9 Hz, 1H), 7.26-7.20 (m, 2H), 7.12 (s, 1H), 7.00-6.97 (m, 1H), 6.26 (d, J = 5.4 Hz, 1H), 4.23 (t, J = 6.6 Hz, 1H), 3.51-3.37 (m, 2H), 2.58 (d, J = 6.7 Hz, 2H), 2.34 (d, J = 1.0 Hz, 3H), 2.14-2.12 (m, 9H), 2.02-2.02 (m, 2H). | Rt = 3.03 min, m/z 394.2 [M + H]+ (Method 1) |
| 6 | 3-amino-N-(3-methoxypropyl)-3-(3-((3-methyl-1H-pyrrolo[2,3-b]pyridin-4-yl)oxy)phenyl)propanamide | 1E-b/3-methoxy-propylamine | $^1$H NMR (400 MHz, d6-DMSO) δ 11.35 (s, 1H), 7.99 (d, J = 5.4 Hz, 1H), 7.88 (t, J = 5.6 Hz, 1H), 7.36 (t, J = 7.9 Hz, 1H), 7.24-7.12 (m, 3H), 6.99-6.96 (m, 1H), 6.24 (d, J = 5.4 Hz, 1H), 4.20 (t, J = 6.9 Hz, 1H), 3.23 (t, J = 6.4 Hz, 2H), 3.18 (s, 3H), 3.07-2.99 (m, 2H), 2.35-2.32 (m, 5H), 2.04-2.00 (m, 2H), 1.57-1.52 (m, 2H). | Rt = 1.99 min, m/z 383.2 [M + H]+ (Method 1) |
| 7 | 3-amino-3-(3-((3-methyl-1H-pyrrolo[2,3-b]pyridin-4-yl)oxy)phenyl)-N-(2-(pyridin-4-yl)ethyl)propanamide | 1E-b/2-(4-pyridyl)-ethylamine | $^1$H NMR (400 MHz, d6-DMSO) δ 11.35 (s, 1H), 8.43 (d, J = 6.0 Hz, 2H), 8.02 (t, J = 5.7 Hz, 1H), 7.98 (d, J = 5.3 Hz, 1H), 7.37 (t, J = 7.9 Hz, 1H), 7.23-7.10 (m, 5H), 6.99 (dd, J = 1.7, 7.9 Hz, 1H), 6.23 (d, J = 5.4 Hz, 1H), 4.19 (t, J = 6.9 Hz, 1H), 4.09 (ddd, J = 5.2, 5.2, 5.2 Hz, 1H), 3.31-3.23 (m, 3H), 3.17 (d, J = 5.1 Hz, 3H), 2.66 (t, J = 7.3 Hz, 2H), 1.95 (s, 2H) | Rt = 1.57 min, m/z 416.3 [M + H]+ (Method 1) |
| 8 | 3-amino-N-(3-(dimethylamino)propyl)-3-(3-((3-methyl-1H-pyrrolo[2,3-b]pyridin-4-yl)oxy)phenyl)propanamide | 1E-b/3-(dimethyl-amino)-1-propyl-amine | $^1$H NMR (400 MHz, d6-DMSO) δ 11.35 (s, 1H), 7.99 (d, J = 5.4 Hz, 1H), 7.87 (t, J = 5.6 Hz, 1H), 7.36 (t, J = 7.8 Hz, 1H), 7.24-7.18 (m, 2H), 7.12 (s, 1H), 7.00-6.95 (m, 1H), 6.24 (d, J = 5.4 Hz, 1H), 4.20 (t, J = 6.9 Hz, 1H), 3.04-2.96 (m, 2H), 2.34 (d, J = 0.9 Hz, 3H), 2.33-2.31 (m, 2H), 2.11 (t, J = 7.1 Hz, 2H), 2.07 (s, 6H), 1.98 (s, 2H), 1.48-1.39 (m, 2H). | Rt = 3.03 min, m/z 396.2 [M + H]+ (Method 2) |

| Ex | Structure | Intermediate 1E/Amine | 1H NMR | LC-MS |
|---|---|---|---|---|
| 9 | 3-amino-2-(3-((3-methyl-1H-pyrrolo[2,3-b]pyridin-4-yl)oxy)benzyl)-1-(4-methylpiperazin-1-yl)propan-1-one | 1E-c/1-methyl piperazine | $^1$H NMR (400 MHz, d6-DMSO) δ 11.36 (s, 1H), 8.00 (d, J = 5.4 Hz, 1H), 7.36-7.31 (m, 1H), 7.12 (s, 1H), 7.03 (m, 1H), 6.99-6.90 (m, 2H), 6.23 (d, J = 5.4 Hz, 1H), 3.54-3.49 (m, 1H), 3.27-3.05 (m, 4H), 2.82-2.68 (m, 3H), 2.59-2.52 (m, 1H), 2.33 (d, J = 1.0 Hz, 3H), 2.25-2.16 (m, 2H), 2.06 (s, 3H), 1.96-1.91 (m, 1H), 1.76-1.67 (m, 1H), 1.55-1.49 (m, 2H). | Rt = 1.61 min, m/z 408.3 [M + H]+ (Method 1) |
| 10 | 3-amino-N-(3-methoxypropyl)-2-(3-((3-methyl-1H-pyrrolo[2,3-b]-pyridin-4-yl)oxy)benzyl)propanamide | 1E-c/3-methoxy-propylamine | $^1$H NMR (400 MHz, d6-DMSO) δ 11.35 (s, 1H), 7.99 (d, J = 5.4 Hz, 1H), 7.79 (t, J = 5.6 Hz, 1H), 7.32 (t, J = 7.8 Hz, 1H), 7.11 (s, 1H), 7.04 (d, J = 7.7 Hz, 1H), 6.98-6.92 (m, 2H), 6.23 (d, J = 5.4 Hz, 1H), 3.19-3.16 (m, 2H), 3.15 (s, 3H), 3.13-2.93 (m, 2H), 2.79-2.64 (m, 3H), 2.59-2.52 (m, 1H), 2.47-2.39 (m, 1H), 2.33 (d, J = 0.9 Hz, 3H), 1.54-1.44 (m, 4H). | Rt = 2.17 min, m/z 397.2 [M + H]+ (Method 1) |
| 11 | 3-amino-2-(3-((3-methyl-1H-pyrrolo[2,3-b]pyridin-4-yl)oxy)benzyl)-N-(2-(pyridin-4-yl)ethyl)propanamide | 1E-c/2-(4-pyridyl)-ethylamine | $^1$H NMR (400 MHz, d6-DMSO) δ 11.34 (s, 1H), 8.42-8.39 (m, 2H), 7.97 (d, J = 5.5 Hz, 1H), 7.94 (t, J = 5.7 Hz, 1H), 7.36-7.30 (m, 1H), 7.13-7.07 (m, 3H), 7.05-7.01 (m, 1H), 6.97-6.95 (m, 2H), 6.22 (d, J = 5.5 Hz, 1H), 3.29-3.15 (m, 3H), 2.76-2.53 (m, 6H), 2.46-2.37 (m, 1H), 2.30 (d, J = 0.9 Hz, 3H), 1.47 (s, 1H). | Rt = 1.74 min, m/z 430.3 [M + H]+ (Method 1) |
| 12 | 3-amino-N-(3-(dimethylamino)propyl)-2-(3-((3-methyl-1H-pyrrolo[2,3-b]pyridin-4-yl)oxy)benzyl)propanamide | 1E-c/3-(dimethyl-amino)-1-propyl-amine | $^1$H NMR (400 MHz, d6-DMSO) δ 11.35 (s, 1H), 7.99 (d, J = 5.4 Hz, 1H), 7.78 (t, J = 5.6 Hz, 1H), 7.32 (t, J = 7.8 Hz, 1H), 7.11 (s, 1H), 7.04 (d, J = 7.6 Hz, 1H), 6.99-6.92 (m, 2H), 6.23 (d, J = 5.4 Hz, 1H), 3.06-2.90 (m, 2H), 2.79-2.63 (m, 3H), 2.55 (dd, J = 5.3, 12.5 Hz, 1H), 2.46-2.38 (m, 1H), 2.33 (d, J = 0.9 Hz, 3H), 2.07 (d, J = 7.2 Hz, 2H), 2.04 (s, 6H), 1.44-1.35 (m, 2H). | Rt = 1.66 min, m/z 410.3 [M + H]+ (Method 1) |

Example 13

Step A

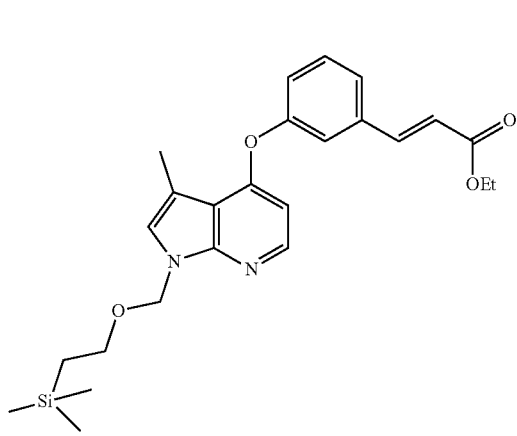 [SMILES: CCOC(=O)/C=C/c1cccc(Oc2ccnc3c2c(C)cn3COCC[Si](C)(C)C)c1]

Ethyl (E)-3-(3-((3-methyl-1-((2-(trimethylsilyl)
ethoxy)methyl)-1H-pyrrolo[2,3-b]pyridin-4-yl)oxy)
phenyl)acrylate (Intermediate 13A)

Intermediate 13A was prepared from Intermediate 1C-a and ethyl (E)-3-(3-hydroxyphenyl)acrylate using a similar procedure to that used in Step D of Example 1.

LCMS (Method 4): Rt=1.92 min, m/z 453.3 [M+H]$^+$

Step B

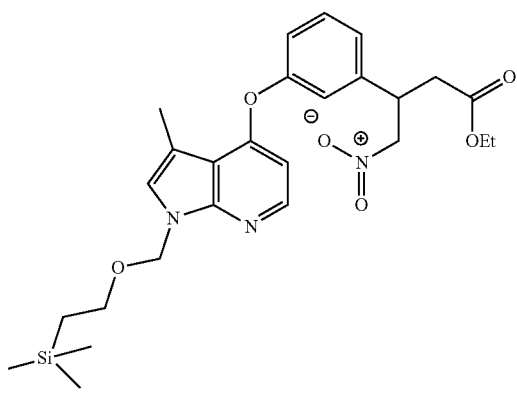 [SMILES: CCOC(=O)CC(C[N+](=O)[O-])c1cccc(Oc2ccnc3c2c(C)cn3COCC[Si](C)(C)C)c1]

Ethyl 3-(3-((3-methyl-1-((2-(trimethylsilyl)ethoxy)
methyl)-1H-pyrrolo[2,3-b]pyridin-4-yl)oxy)phenyl)-
4-nitrobutanoate (Intermediate 13B)

A solution of Intermediate 13A (500 mg, 1.1 mmol) in nitromethane (10 mL) was chilled (ice/water) and treated with DBU (0.166 mL, 1.11 mmol added dropwise over 10 min). The reaction mixture was stirred cold for 30 min then without cooling for a further 5.5 h. The mixture was added to water (75 mL) then extracted with ethyl acetate (2×50 mL). The combined organic phase was washed with water and saturated brine then dried (MgSO$_4$) and concentrated to afford the crude product. The crude product was purified on a 25 g Si cartridge eluting with 0-75% ethyl acetate in cyclohexane to give the desired product a colourless oil (0.48 g).

LCMS (Method 4): Rt=1.80 min, m/z 514.3 [M+H]$^+$

Step C

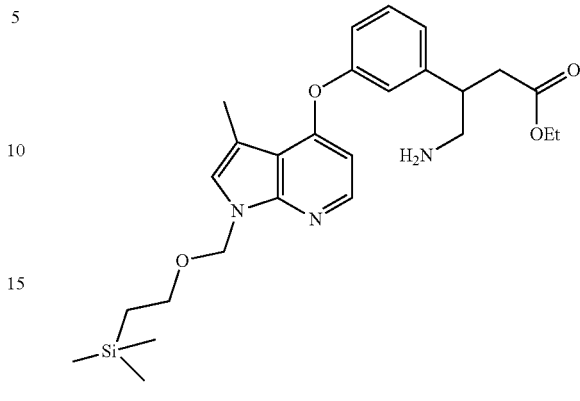

Ethyl 4-amino-3-(3-((3-methyl-1-((2-(trimethylsilyl)
ethoxy)methyl)-1H-pyrrolo-[2,3-b]pyridin-4-yl)oxy)
phenyl)butanoate (Intermediate 13C)

A stirred and chilled mixture of intermediate 13B (0.48 g, 0.93 mmol) and nickel (II) chloride hexahydrate (0.233 g, 0.93 mmol) in methanol (30 mL) was treated with sodium borohydride (0.426 g, 11 mmol, added portion-wise during 10 min). The mixture was stirred cold (0-5° C.) for a further 1 h then treated with saturated ammonium chloride (200 mL). The resultant mixture was extracted with DCM (3×50 mL). The combined organic phase was dried (Na$_2$SO$_4$) and concentrated to afford the crude product (0.48 g) intermediate 13C-a. No further purification was undertaken with this material.

LCMS (Method 4): Rt=1.22 min, m/z 484.3 [M+H]$^+$

Step D

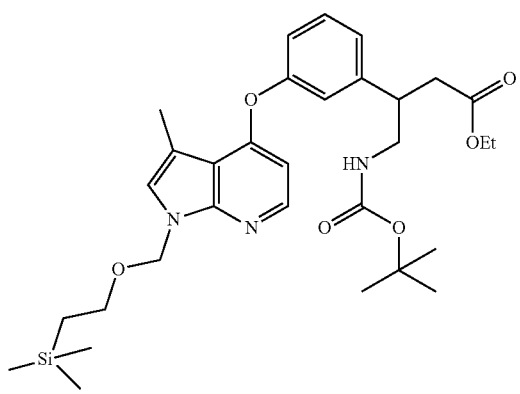 [SMILES: CCOC(=O)CC(CNC(=O)OC(C)(C)C)c1cccc(Oc2ccnc3c2c(C)cn3COCC[Si](C)(C)C)c1]

Ethyl 4-((tert-butoxycarbonyl)amino)-3-(3-((3-
methyl-1-((2-(trimethylsilyl)-ethoxy)methyl)-1H-
pyrrolo[2,3-b]pyridin-4-yl)oxy)phenyl)butanoate
(Intermediate 13D)

A solution of di-tert-butyl dicarbonate (422 mg, 1.93 mmol) in DCM (10 mL) was added to a chilled (ice/water bath) solution of intermediate 13C (0.85 g, 1.76 mmol) and triethylamine (0.49 mL, 3.51 mmol) in DCM (30 mL). The mixture was stirred cold for 30 minutes then added to water and the phases were separated. The aqueous phase was extracted with DCM. The combined organic phase was washed with water and brine then dried ($Na_2SO_4$). Concentration gave the crude product which was purified on a 25 g Si cartridge eluting with 0-100% ethyl acetate in cyclohexane to afford intermediate 13D-a a colourless oil (0.70 g).

LCMS (Method 4): Rt=1.91 min, m/z 584.3 $[M+H]^+$

Step E

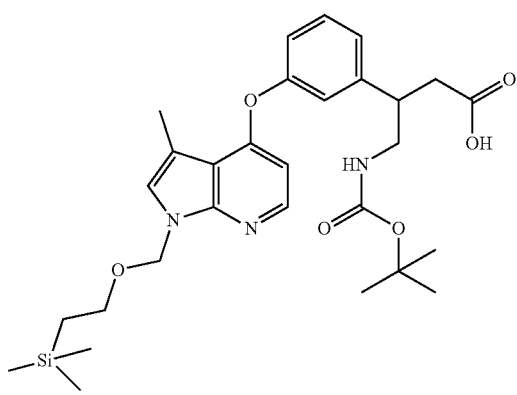 [SMILES: Cc1cn(COCC[Si](C)(C)C)c2nccc(Oc3cccc(C(CNC(=O)OC(C)(C)C)CC(=O)O)c3)c12]

4-((tert-butoxycarbonyl)amino)-3-(3-((3-methyl-1-((2-(trimethylsilyl)ethoxy)methyl)-1H-pyrrolo[2,3-b]pyridin-4-yl)oxy)phenyl)butanoic Acid (Intermediate 13E)

A solution of lithium hydroxide monohydrate (100 mg, 2.38 mmol) in water (5 mL) was added to a mixture of intermediate 13D (0.70 g, 1.2 mmol) in THF (15 mL) and water (10 mL). The mixture was stirred for 18 h then concentrated in vacuo to remove most of the organic solvent. The resulting solution was acidified (1M hydrochloric acid) and extracted with ethyl acetate (3×40 mL). The combined organic phase was washed with sodium bicarbonate solution and saturated brine then dried ($Na_2SO_4$) and concentrated in vacuo to afford intermediate 13E-a, a colourless gum (0.66 g).

LCMS (Method 4): Rt=1.74 min, m/z 556.3 $[M+H]^+$

Step F

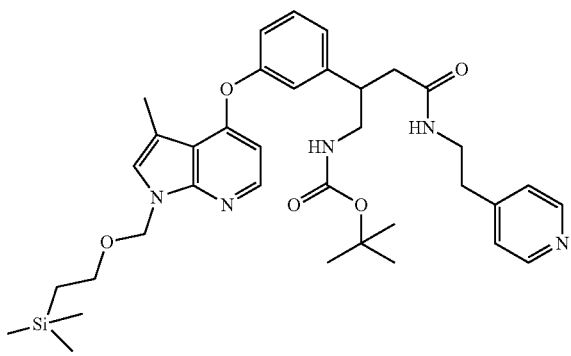 [SMILES: Cc1cn(COCC[Si](C)(C)C)c2nccc(Oc3cccc(C(CNC(=O)OC(C)(C)C)CC(=O)NCCc4ccncc4)c3)c12]

tert-Butyl (2-(3-((3-methyl-1-((2-(trimethylsilyl)ethoxy)methyl)-1H-pyrrolo[2,3-b]pyridin-4-yl)oxy)phenyl)-4-oxo-4-((2-(pyridin-4-yl)ethyl)amino)butyl)carbamate (Intermediate 13F)

Intermediate 13F was prepared from Intermediate 13E and 2-(4-pyridyl)ethylamine using a similar procedure to that used in Step F of Example 1.

LCMS (Method 4): Rt=1.34 min, m/z 660.5 $[M+H]^+$

Step G

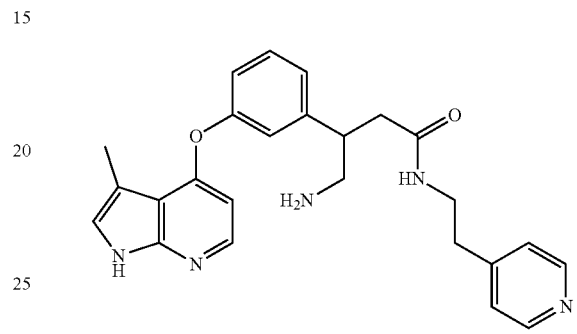

4-Amino-3-(3-((3-methyl-1H-pyrrolo[2,3-b]pyridin-4-yl)oxy)phenyl)-N-(2-(pyridin-4-yl)ethyl)butanamide (Example 13)

A mixture of intermediate 13F (170 mg, 0.26 mmol), DCM (1.5 mL) and TFA (1.0 mL) was stirred at ambient temperature for 2.5 h. The mixture was then loaded onto a 5 g SCX 2 cartridge. The cartridge was eluted with methanol then with 2M methanolic ammonia. The basic fraction was concentrated and the residue purified by MDAP to afford a colourless glass. This was freeze-dried from acetonitrile/water/formic acid to give a white solid which was triturated with acetonitrile three times. The solid was then taken into DCM with minimum methanolic ammonia and further purified by chromatography on a 4 g Si cartridge eluting with 0-10% 2M methanolic ammonia in DCM. Appropriate fractions were concentrated in vacuo and freeze-dried from acetonitrile/water to afford Example 13 (16.8 mg).

LCMS (Method 1): Rt=1.55 min, m/z 430.2 $[M+H]^+$ $^1$H NMR (400 MHz, d6-DMSO) δ 11.34 (s, 1H), 8.41 (d, J=5.9 Hz, 7.96 (d, J=5.4 Hz, 1H), 7.89-7.85 (m, 1H), 7.36 (t, J=7.8 Hz, 1H), 7.12-7.05 (m, 4H), 6.99-6.95 (m, 2H), 6.22 (d, J=5.4 Hz, 1H), 3.28-3.16 (m, 3H), 3.09-2.99 (m, 1H), 2.68 (d, J=6.9 Hz, 2H), 2.63-2.57 (m, 2H), 2.33-2.31 (m, 3H), 2.30-2.24 (m, 1H), 1.80 (s, 2H).

Preparation of Examples 14 to 16

The following examples were prepared in a similar manner to Example 13 from intermediate 13E, following the same synthetic sequence, by replacing in Step F the indicated amine starting materials in the table below.

| Ex | Structure | Amine | 1H NMR | LC-MS |
|---|---|---|---|---|
| 14 | 4-amino-N-(3-methoxypropyl)-3-(3-((3-methyl-1H-pyrrolo[2,3-b]pyridin-4-yl)oxy)phenyl)butanamide | 3-Methoxypropyl-amine | $^1$H NMR (400 MHz, d6-DMSO) δ 11.36 (s, 1H), 7.98 (d, J = 5.4 Hz, 1H), 7.75 (t, J = 5.7 Hz, 1H), 7.36 (t, J = 7.8 Hz, 1H), 7.13-7.06 (m, 2H), 7.01-6.94 (m, 2H), 6.22 (d, J = 5.4 Hz, 1H), 3.15 (s, 3H), 3.14-3.11 (m, 2H), 3.08-2.91 (m, 4H), 2.69 (d, J = 6.8 Hz, 2H), 2.33 (d, J = 0.9 Hz, 3H), 2.28 (m, 1H), 1.70 (s, 2H), 1.50-1.43 (m, 2H). | Rt = 2.00 min, m/z 397.2 [M + H]+ (Method 1) |
| 15 | 4-amino-N-(3-(dimethylamino)propyl)-3-(3-((3-methyl-1H-pyrrolo[2,3-b]pyridin-4-yl)oxy)phenyl)butanamide | 3-(Dimethylamino)-1-propylamine | $^1$H NMR (400 MHz, d6-DMSO) δ 11.33 (s, 1H), 7.98 (d, J = 5.4 Hz, 1H), 7.72 (t, J = 5.6 Hz, 1H), 7.35 (t, J = 7.8 Hz, 1H), 7.13-7.10 (m, 1H), 7.08 (d, J = 7.5 Hz, 1H), 7.01-6.98 (m, 1H), 6.95 (dd, J = 2.3, 7.9 Hz, 1H), 6.23 (d, J = 5.5 Hz, 1H), 3.16-2.90 (m, 6H), 2.70 (d, J = 6.8 Hz, 2H), 2.33 (d, J = 0.7 Hz, 3H), 2.04-2.03 (m, 9H), 1.42-1.32 (m, 2H). | Rt = 3.00 min, m/z 410.3 [M + H]+ (Method 2) |
| 16 | 4-amino-3-(3-((3-methyl-1H-pyrrolo[2,3-b]pyridin-4-yl)oxy)phenyl)-1-(4-methyl-piperazin-1-yl)butan-1-one | 1-Methylpiperazine | $^1$H NMR (400 MHz, d6-DMSO) δ 11.36 (s, 1H), 7.99 (d, J = 5.4 Hz, 1H), 7.35 (t, J = 7.9 Hz, 1H), 7.13-7.09 (m, 2H), 7.04-7.02 (m, 1H), 6.95 (dd, J = 2.0, 7.8 Hz, 1H), 6.24 (d, J = 5.4 Hz, 1H), 3.44-3.36 (m, 4H), 3.08-3.01 (m, 1H), 2.75-2.69 (m, 3H), 2.62 (dd, J = 8.8, 15.3 Hz, 1H), 2.33 (d, J = 1.0 Hz, 3H), 2.25-2.15 (m, 2H), 2.11 (s, 3H), 2.10-2.02 (m, 2H), 1.66 (s, 2H). | Rt = 2.99 min, m/z 408.2 [M + H]+ (Method 2) |

Pharmacological Activity of the Compounds of the Invention

In Vitro Inhibitory Activity Assay Description

The effectiveness of compounds of the invention to inhibit Rho kinase activity can be determined in a 10 μl assay containing 40 mM Tris pH7.5, 20 mM MgCl$_2$, 0.1 mg/ml BSA, 50 μM DTT and 2.5 μM peptide substrate (Myelin Basic Protein) using an ADP-Glo kit (Promega). Compounds were dissolved in DMSO such that the final concentration of DMSO was 1% in the assay. All reactions/incubations are performed at 25° C. Compound (2 ul) and either Rho kinase 1 or 2 (4 μl) were mixed and incubated for 30 mins. Reactions were initiated by addition of ATP (4 μl) such that the final concentration of ATP in the assay was 10 μM. After a 1 hour incubation 10 μl of ADP-Glo Reagent was added and after a further 45 minute incubation 20 ul of Kinase Detection Buffer was added and the mixture incubated for a further 30 minutes. The luminescent signal was measured on a luminometer. Controls consisted of assay wells that did not contain compound with background determined using assay wells with no enzyme added. Compounds were tested in dose-response format and the inhibition of kinase activity was calculated at each concentration of compound. To determine the IC$_{50}$ (concentration of compound required to inhibit 50% of the enzyme activity) data were fit to a plot of % inhibition vs Log$_{10}$ compound concentration using a sigmoidal fit with a variable slope and fixing the maximum to 100% and the minimum to 0%. To determine the Ki values the Cheng-Prusoff equation was utilized (Ki=IC$_{50}$/(1+[S]/Km)

Compounds according to the invention showed Ki values lower than 5 μM and for most of the compounds of the invention Ki is even lower that 500 nM.

The results for individual compounds are provided below in Table 1 and are expressed as range of activity.

TABLE 1

| Example | Activity ROCK1 | Activity ROCK2 |
|---|---|---|
| 1 | ++ | ++ |
| 2 | ++ | ++ |
| 3 | + | + |
| 4 | +++ | +++ |
| 5 | ++ | ++ |
| 6 | ++ | ++ |
| 7 | ++ | ++ |
| 8 | + | + |
| 9 | + | + |

| Example | Activity ROCK1 | Activity ROCK2 |
| --- | --- | --- |
| 10 | ++ | ++ |
| 11 | ++ | ++ |
| 12 | + | + |
| 13 | ++ | ++ |
| 14 | ++ | ++ |
| 15 | + | + |
| 16 | ++ | ++ | wherein the compounds are classified in term of potency with respect to their inhibitory activity on ROCK 1 ROCK 2 isoforms according to the following classification criterion:

+++: Ki<5 nM
++: Ki in the range 5-50 nM
+: Ki>50 nM.

The invention claimed is:

1. A compound of formula (I)

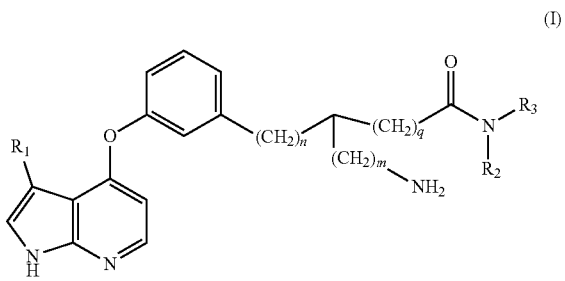

wherein
n, q and m are zero or an integer from 1 to 2;
$R_1$ is selected from the group consisting of
—H,
halogen,
—CN,
$(C_1\text{-}C_6)$ alkyl,
$R_2$ and $R_3$, the same or different, are selected from the group consisting of
—H,
$(C_1\text{-}C_6)$ alkyl,
$(C_1\text{-}C_6)$ haloalkyl,
$(C_1\text{-}C_6)$ hydroxyalkyl,
$(C_1\text{-}C_6)$ aminoalkyl,
$(C_1\text{-}C_6)$ alkoxy $(C_1\text{-}C_6)$ alkyl,
heteroaryl$(C_1\text{-}C_6)$alkyl,
each of said heteroaryl is further optionally substituted by one or more group selected independently from halogen, —CN, —OH, $(C_1\text{-}C_8)$alkyl, $(C_1\text{-}C_6)$ haloalkyl, $(C_1\text{-}C_{10})$alkoxy, aryl, aryl$(C_1\text{-}C_6)$alkyl, carbamoyl, $(C_1\text{-}C_6)$ aminoalkyl, $(C_1\text{-}C_6)$ hydroxyalkyl; or alternatively,
$R_2$ and $R_3$, taken together with the nitrogen atom they are linked to, form a mono-cyclic saturated or partially saturated heterocyclic radical, wherein at least one further ring carbon atom is optionally replaced by N,
said heterocyclic radical being optionally in its turn further substituted with one or more $(C_1\text{-}C_6)$ alky groups;
or pharmaceutically acceptable salts and solvates thereof.

2. A compound according to claim 1, wherein
n, q and m are zero or 1;
$R_1$ is $(C_1\text{-}C_6)$ alkyl,
$R_2$ and $R_3$, the same or different, are selected from the group consisting of:
—H,
$(C_1\text{-}C_6)$ aminoalkyl,
$(C_1\text{-}C_6)$ alkoxy $(C_1\text{-}C_6)$ alkyl,
heteroaryl$(C_1\text{-}C_6)$alkyl,
or alternatively,
$R_2$ and $R_3$, taken together with the nitrogen atom they are linked to, form a mono-cyclic saturated or partially saturated heterocyclic radical, wherein at least one further ring carbon atom is optionally replaced by N,
said heterocyclic radical being optionally in its turn further substituted with one or more $(C_1\text{-}C_6)$ alkyl groups.

3. A compound according to claim 1, wherein
n, q and m are zero or 1;
$R_1$ is methyl,
$R_2$ and $R_3$, the same or different, are selected from the group consisting of:
—H,
dimethylaminopropyl,
methoxypropyl,
pyridinylethyl;
or alternatively,
$R_2$ and $R_3$, taken together with the nitrogen atom they are linked to, form a mono-cyclic 6-membered saturated or partially saturated heterocyclic radical, wherein at least one further ring carbon atom is optionally replaced by N,
said heterocyclic radical being optionally in its turn further substituted with one or more methyl groups.

4. A compound according to claim 1, wherein
n, q and m are zero or 1;
$R_1$ is methyl,
$R_2$ and $R_3$, the same or different, are selected from the group consisting of:
—H,
methoxypropyl,
pyridinylethyl;
or alternatively,
$R_2$ and $R_3$, taken together with the nitrogen atom they are linked to, form a mono-cyclic 6-membered saturated or partially saturated heterocyclic radical, wherein at least one further ring carbon atom is optionally replaced by N, substituted with one methyl group.

5. A compound according to claim 1 selected from:
2-amino-3-(3-((3-methyl-1H-pyrrolo[2,3-b]pyridin-4-yl)oxy)phenyl)-1-(4-methylpiperazin-1-yl)propan-1-one;
2-amino-N-(3-methoxypropyl)-3-(3-((3-methyl-1H-pyrrolo[2,3-b]pyridin-4-yl)oxy)phenyl)propanamide;
2-amino-N-(3-(dimethylamino)propyl)-3-(3-((3-methyl-1H-pyrrolo[2,3-b]pyridin-4-yl)oxy)phenyl)propanamide;
2-amino-3-(3-((3-methyl-1H-pyrrolo[2,3-b]pyridin-4-yl)oxy)phenyl)-N-(2-(pyridin-4-yl)ethyl)propanamide;
3-amino-3-(3-((3-methyl-1H-pyrrolo[2,3-b]pyridin-4-yl)oxy)phenyl)-1-(4-methylpiperazin-1-yl)propan-1-one;
3-amino-N-(3-methoxypropyl)-3-(3-((3-methyl-1H-pyrrolo[2,3-b]pyridin-4-yl)oxy)phenyl)propanamide;
3-amino-3-(3-((3-methyl-1H-pyrrolo[2,3-b]pyridin-4-yl)oxy)phenyl)-N-(2-(pyridin-4-yl)ethyl)propanamide;
3-amino-N-(3-(dimethylamino)propyl)-3-(3-((3-methyl-1H-pyrrolo[2,3-b]pyridin-4-yl)oxy)phenyl)propanamide;

3-amino-2-(3-((3-methyl-1H-pyrrolo[2,3-b]pyridin-4-yl) oxy)benzyl)-1-(4-methylpiperazin-1-yl)propan-1-one;
3-amino-N-(3-methoxypropyl)-2-(3-((3-methyl-1H-pyrrolo[2,3-b]pyridin-4-yl)oxy)benzyl)propanamide;
3-amino-2-(3-((3-methyl-1H-pyrrolo[2,3-b]pyridin-4-yl) oxy)benzyl)-N-(2-(pyridin-4-yl)ethyl)propanamide;
3-amino-N-(3-(dimethylamino)propyl)-2-(3-((3-methyl-1H-pyrrolo[2,3-b]pyridin-4-yl)oxy)benzyl)propanamide;
4-amino-3-(3-((3-methyl-1H-pyrrolo[2,3-b]pyridin-4-yl) oxy)phenyl)-N-(2-(pyridin-4-yl)ethyl)butanamide;
4-amino-N-(3-methoxypropyl)-3-(3-((3-methyl-1H-pyrrolo[2,3-b]pyridin-4-yl)oxy)phenyl)butanamide;
4-amino-N-(3-(dimethylamino)propyl)-3-(3-((3-methyl-1H-pyrrolo[2,3-b]pyridin-4-yl)oxy)phenyl)butanamide;
4-amino-3-(3-((3-methyl-1H-pyrrolo[2,3-b]pyridin-4-yl) oxy)phenyl)-1-(4-methylpiperazin-1-yl)butan-1-one;
or pharmaceutically acceptable salts and solvates thereof.

6. A pharmaceutical composition comprising a compound as defined in claim 1, or a pharmaceutically acceptable salt thereof, either alone or in combination with another one or more active ingredients, in admixture with one or more pharmaceutically acceptable carriers or excipients.

7. A pharmaceutical composition according to claim 6 suitable to be administered by inhalation.

8. A combination of a compound as defined in claim 1 with one or more active ingredients selected from the classes consisting of organic nitrates and NO donors; inhaled NO; stimulators of soluble guanylate cyclase (sGC); prostaciclin analogue PGI2 and agonist of prostacyclin receptors; compounds that inhibit the degradation of cyclic guanosine monophosphate (cGMP) and/or cyclic adenosine monophosphate (cAMP); human neutrophilic elastase inhibitors; compounds inhibiting the signal transduction cascade; active substances for lowering blood pressure; neutral endopeptidase inhibitors; osmotic agents; ENaC blockers; anti-inflammatories including corticosteroids and antagonists of chemokine receptors; bronchodilators; antihistamine drugs; anti-tussive drugs; antibiotics and DNase drug substances and selective cleavage agents; agents that inhibit ALK5 and/or ALK4 phosphorylation of Smad2 and Smad3; tryptophan hydroylase 1 (TPH1) inhibitors and multi-kinase inhibitors.

9. A device comprising the pharmaceutical composition according to claim 6, wherein the device is a single- or multi-dose dry powder inhaler, a metered dose inhaler, or a soft mist nebulizer.

10. A pharmaceutical composition comprising a compound as defined in claim 5, or a pharmaceutically acceptable salt thereof, either alone or in combination with another one or more active ingredients, in admixture with one or more pharmaceutically acceptable carriers or excipients.

11. A pharmaceutical composition according to claim 10 suitable to be administered by inhalation.

12. A combination of a compound as defined in claim 5 with one or more active ingredients selected from the classes consisting of organic nitrates and NO donors; inhaled NO; stimulators of soluble guanylate cyclase (sGC); prostaciclin analogue PGI2 and agonist of prostacyclin receptors; compounds that inhibit the degradation of cyclic guanosine monophosphate (cGMP) and/or cyclic adenosine monophosphate (cAMP); human neutrophilic elastase inhibitors; compounds inhibiting the signal transduction cascade; active substances for lowering blood pressure; neutral endopeptidase inhibitors; osmotic agents; ENaC blockers; anti-inflammatories including corticosteroids and antagonists of chemokine receptors; bronchodilators; antihistamine drugs; anti-tussive drugs; antibiotics and DNase drug substances and selective cleavage agents; agents that inhibit ALK5 and/or ALK4 phosphorylation of Smad2 and Smad3; tryptophan hydroylase 1 (TPH1) inhibitors and multi-kinase inhibitors.

13. A device comprising the pharmaceutical composition according to claim 10, wherein the device is a single- or multi-dose dry powder inhaler, a metered dose inhaler, or a soft mist nebulizer.

* * * * *